(12) United States Patent
Sakairi et al.

(10) Patent No.: US 6,571,649 B2
(45) Date of Patent: Jun. 3, 2003

(54) EXPLOSIVE DETECTION SYSTEM AND SAMPLE COLLECTING DEVICE

(75) Inventors: Minoru Sakairi, Tokorozawa (JP); Masao Suga, Hachiouji (JP); Yuichiro Hashimoto, Kokubunji (JP); Masuyoshi Yamada, Ichikawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/884,089

(22) Filed: Jun. 20, 2001

(65) Prior Publication Data

US 2001/0042413 A1 Nov. 22, 2001

Related U.S. Application Data

(63) Continuation of application No. 09/348,565, filed on Jul. 7, 1999, now Pat. No. 6,295,860.

(30) Foreign Application Priority Data

Jul. 8, 1998 (JP) .......................................... 10-192662

(51) Int. Cl.[7] ................................................. G01N 1/00
(52) U.S. Cl. .................................................... 73/863.21
(58) Field of Search ......................... 73/863.11, 863.12, 73/863.21, 863.23–863.25, 864.73

(56) References Cited

U.S. PATENT DOCUMENTS

| | | | | | |
|---|---|---|---|---|---|
| 4,779,466 | A | * | 10/1988 | Ramsner et al. | 73/863.24 |
| 4,909,090 | A | * | 3/1990 | McGown et al. | 73/863.12 |
| 5,039,322 | A | * | 8/1991 | Holzl | 73/863.24 |
| 5,092,157 | A | * | 3/1992 | Achter et al. | 73/863.12 |
| 5,456,104 | A | * | 10/1995 | Rosen | 73/863.11 |
| 5,824,919 | A | * | 10/1998 | Hansen | 73/863.12 |
| 6,293,161 | B1 | * | 9/2001 | Hanashiro et al. | 73/863.11 |

* cited by examiner

Primary Examiner—Robert Raevis
(74) Attorney, Agent, or Firm—Antonelli, Terry, Stout & Kraus, LLP

(57) ABSTRACT

A sample introduction probe for introducing a gas sample to a mass spectrometer, having an inner pipe for conducting the sample to be analyzed, and an outer pipe installed outside of the inner pipe. An opening is installed at one end of the inner pipe for enabling entry of the sample into the inner pipe. A pump is installed on a side of the one end of the inner pipe, and a probe tip heater is provided for heating the one end of the inner pipe, a heater for heating the inner pipe.

10 Claims, 20 Drawing Sheets

RDX ically ionizing procedure based on corona discharge.
EXPLOSIVE DETECTION SYSTEM AND SAMPLE COLLECTING DEVICE

CROSS REFERENCE TO RELATED APPLICATION

This is a continuation of U.S. application Ser. No. 09/348,565, filed Jul. 7, 1999, now U.S. Pat. No. 6,295,860, the subject matter of which is incorporated by reference herein.

BACKGROUND OF THE INVENTION

The present invention relates to an explosive detection system, and specifically to an explosive detection system for detecting vapor generated from an explosive or the like sensitively to judge whether or not such an explosive is present in luggage, cargo or the like.

As techniques in the prior art for detecting an explosive, the typical example of which is a nitrocompound, to judge whether or not there is such an explosive, there are known methods disclosed in U.S. Pat. Nos. 4,987,767 and 5,109,691. These methods include the steps of collecting vapor from a person or an object to be inspected, concentrating the gas chemically, heating and desorbing the gas, and examining the gas using a detector, such as an ion mobility analyzer or a gas chromatograph having an electron capture detector.

On the other hand, U.S. Pat. Nos. 4,580,440 and 4,718,268 disclose a mass spectrometer using an atmosphere-chemically ionizing procedure based on corona discharge. This method includes the steps of concentrating a sample gas chemically, heating and desorbing the gas, and examining the gas with an atmospheric pressure chemical ionization quadrupole mass spectrometer.

In the approaches disclosed in the U.S. Pat. Nos. 4,987,767 and 5,109,691, the sensitivity of the used detector is insufficient. Thus, it is necessary for a detection to be made via the step of chemical concentration. However, if the step of chemical concentration is added, the time required for the chemical concentration, which depends on the degree of the concentration, becomes substantial (several minutes several tens of minutes). For this reason, much time is required for a single analysis, resulting in a problem that it is impossible to carry out continuous and speedy analysis of a lot of specimens. Therefore, there arises a problem in that detection of any explosive inside luggage or cargo at an airport, which is required to be quickly carried out, cannot be realized. How to collect a sample gas from luggage or cargo is also brought into question.

In the approaches disclosed in the U.S. Pat. Nos. 4,580,440 and 4,718,268, a high-sensitivity detector is used, such as an atmospheric pressure ionization mass spectrometer using corona discharge. However, a sufficient capability cannot be exhibited by such a device, so that the step of concentration must be used. Thus, it is impossible to examine a lot of specimens continuously and quickly. In the same manner as in the prior art described above, therefore, there remains a problem in that detection of any explosive inside luggage or cargo at an airport, which is required to be quickly carried out, cannot be realized.

The reason why continuous and speedy examination cannot be achieved in the prior art disclosed in the U.S. Pat. Nos. 4,580,440 and 4,718,268 is as follows. As illustrated in FIG. 13 in the U.S. Pat. No. 4,580,440, firstly, a method is employed in which a sample gas is introduced from a concentration device 62 into an introduction region 102. Thus, much time is required for concentration, heating and desorption of the sample so that the sample gas cannot be introduced continuously and quickly from the specimen. Therefore, this method cannot be applied to detection of any explosive inside luggage and cargo at an airport. Secondly, when the sample gas is introduced from the concentration device 62 into the introduction region 62, the concentration of the sample gas itself introduced into the introduction region 102 is lowered because of abrupt diffusion, which occurs because the volume of the introduction region 102 itself is abruptly enlarged. As a result thereof, there remains a problem in that the detection sensitivity is lowered. Thirdly, the sample gas is not heated in the chamber 102 (the method for heating the sample gas introduced into the chamber 102 is not sufficiently disclosed), and there remains a problem in that the ionization efficiency by corona discharge is bad. Fourthly, the direction of introduction of the sample gas to an orifice 110 for introducing ions into an evacuated mass analyzing region is not sufficiently considered, resulting in a problem in that both the ionization efficiency in a corona discharge region and the efficiency of taking in ions from the orifice 110 are bad. After all, the poor ionization efficiency by corona discharge, as described above, results in the following: the ionization efficiency must be raised by adding a reaction gas (poisonous hydrogen chloride, and the like) from a chemical reaction gas source 100. The fact that poisonous hydrogen chloride is used in inspection of luggage at an airport is very undesirable.

Furthermore, for explosive-detection the publications described above disclose only independent use of a gas detection system. The improvement in detection efficiency of an explosive by combining a gas detection system with an X-ray inspection system or the like has not been investigated. Moreover, the connection of the system in the prior art to any X-ray inspection system is actually difficult since continuous and speedy inspections cannot be carried out.

SUMMARY OF THE INVENTION

In order to solve the above-mentioned problems, the explosive detection system of the present invention comprises a sample introduction region for introducing a gas sample to be inspected, a corona discharge region for corona-discharging the introduced gas sample negatively, and a mass analyzing region for subjecting the ions generated by the corona discharge region to mass analysis. That is, according to the present invention, the fact that explosives, the typical example of which is a nitrocompound, are liable to be ionized negatively is used, and they are ionized by negative corona discharge. The generated negative ions are measured by a mass spectrometer. Since the negative ionization efficiency exhibited by the negative corona discharge is very high, the detection sensitivity is also sufficiently high. For this reason, any complicated chemical concentration step, as in the above-mentioned prior art, becomes unnecessary. By using, in particular, an ion trap mass spectrometer, which is a mass spectrometer including an ion-storing capability, high-speed physical concentration can be used in the mass analyzing region, instead of chemical concentration. High-sensitivity detection can be made without any loss of performance of high-speed detection.

On the other hand, in order to make continuous and speedy inspections by using an atmospheric pressure chemical ionization mass spectrometer, a pipe or the like which can be heated is used so as to forward vapor from a specimen (that is, a sample gas) continuously to an ionization region in the corona discharge region using a gas forwarding pump. At this time, in order to reduce absorption or the like of the sample gas in the pipe unit, a great deal of gas must be introduced at a high speed into the ionization region.

In accordance with the present invention, a mechanism is provided for preventing the gas temperature of the corona discharge region from being lowered and for heating the sample gas efficiently. The drop in the concentration of the sample gas in the corona discharge region is suppressed by setting the volume of the inside of the ionization region so as not to be significantly larger than that of the pipe and further causing the sample gas to be efficiently introduced into a corona discharge space without diffusion. Furthermore, if the flow of the introduced gas is made substantially parallel to the line connecting an aperture for taking ions in a vacuum and the corona discharge region, the ionization efficiency is raised and simultaneously the efficiency of introducing the generated ions into the aperture is raised.

Detection sensitivity can be highly improved to make continuous and speedy inspections of specimens possible by raising the ionization efficiency in the corona discharge region in the above-mentioned manner. The use of any poisonous reaction reagent becomes unnecessary. As a result, the present invention can be applied to inspection of luggage at an airport, and the like. Simultaneously, the present invention can be used together with an X-ray inspection system, so that the capability of inspection and detection of explosives can be improved.

According to the present invention, nitrocompounds having plural nitro groups can be detected with high sensitivity. These nitrocompounds are susceptible to being negatively ionized, and negative ions are easily produced by negative corona discharge. Therefore, very high sensitivity can be attained. Moreover, any sample can be highly concentrated in this mass spectrometer by using, as a mass spectrometer, an ion trap mass spectrometer, inside of which ions can be stored. Therefore, even when the vapor pressure of an object to be inspected, such as an explosive, is very low, an inspection can be certainly made. However, a quadrupole mass spectrometer and a magnetic sector type mass spectrometer can be used as well.

DESCRIPTION OF THE PREFERRED EMBODIMENTS

Embodiment 1

Figure 1:
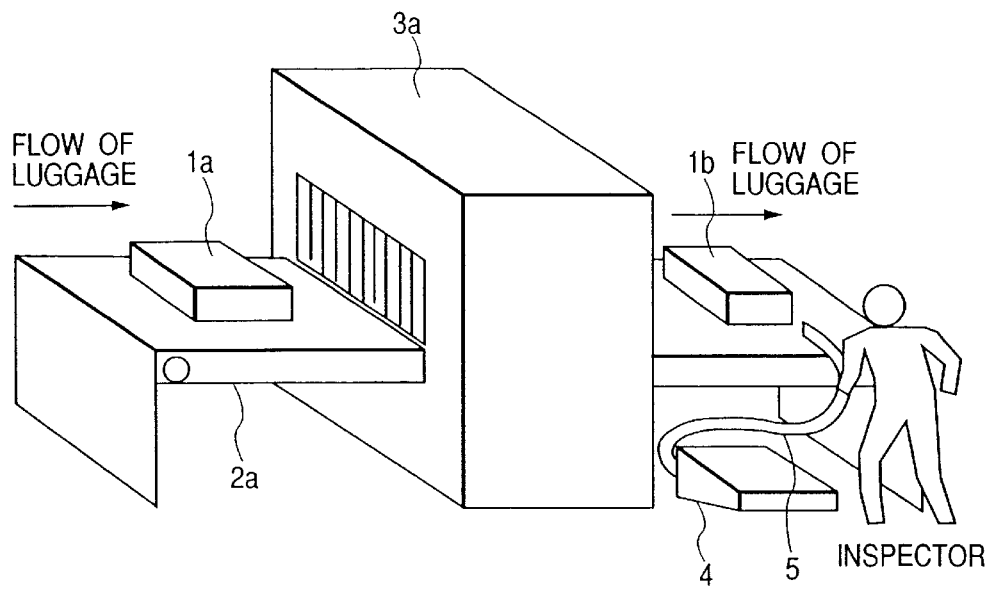
FIG. 1 is a diagrammatic perspective view of an explosive detection system of the present invention.

FIG. 1 illustrates an embodiment of the explosive detection system of the present invention. As will be described later, in accordance with the present invention, the vapor of an explosive, a typical example of which is a nitrocompound, is collected, and subsequently negative corona discharge is used to ionize the vapor. The resultant ions are detected by a mass spectrometer. In the present embodiment, an inspector sucks vapor which leaks from luggage or the like, which is an object to be inspected, with a sampling probe and analyzes the vapor, and then determines whether or not there is an explosive from the analysis results. By using such an approach together with an X-ray inspection system for photographing the form of an explosive element or device inside the luggage from the outside without opening the luggage, the position of the explosive can be checked. On the basis of the detected position, the detection sensitivity can be further improved by bringing the sampling probe close.

Figure 24:
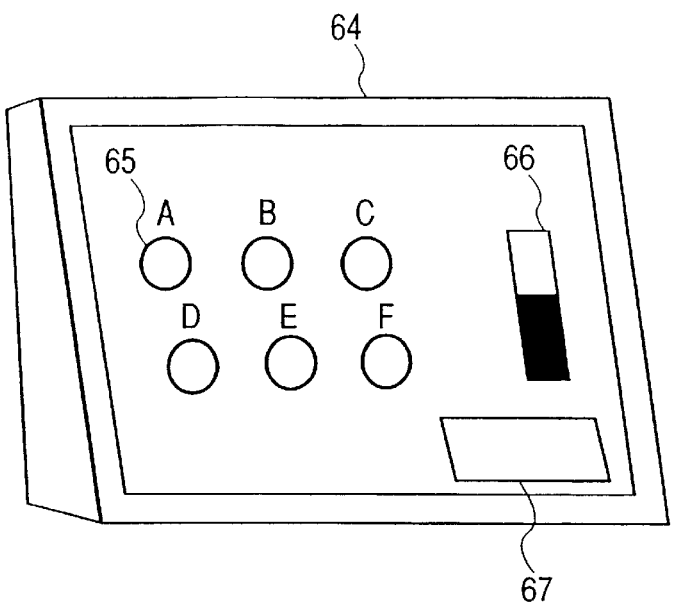
FIG. 24 is a diagram showing an indicating device in an explosive detection system.

The details of the present embodiment will be specifically described, referring to FIG. 1 and the like. Luggage or the like is inspected in public facilities, such as an airport and a port, at the time of embarkation. An object 1a to be inspected, such as a bag, is carried on a belt conveyer 2a to an X-ray inspection system 3a. Luggage 1b subjected to an inspection to detect explosives which have metal components or the like is inspected by an explosive detection system 4 for an off-line analysis for the purpose of detecting the vapor of explosives. In the case illustrated in FIG. 1, an inspector uses a sampling probe 5 for off-line analysis, and brings the probe 5 close to an opening, such as a key hole, of the object 1a to be inspected, such as a bag, or a gap between an upper lid and a lower lid thereof to collect and inspect vapor therein. At this time, if the tip of the sampling probe 5 for off-line analysis is made fine, the vapor inside the bag or the like can be directly collected through the gap. The inspector checks the detection result through an indicating device 64 as shown in FIG. 24. The indicating device 64 has an indicator 65 for a substance corresponding to an ion to be detected. If, for example, substance "A" is detected, it is indicated that substance "A" is detected by turning on and off the indicator "A". In this case, it is permissible to simultaneously provide an indicator 66 and an alarm 67 for indicating the degree of the detected concentration. (As simple information, information as to whether the amount is large or small is permissible.)

Figure 26:
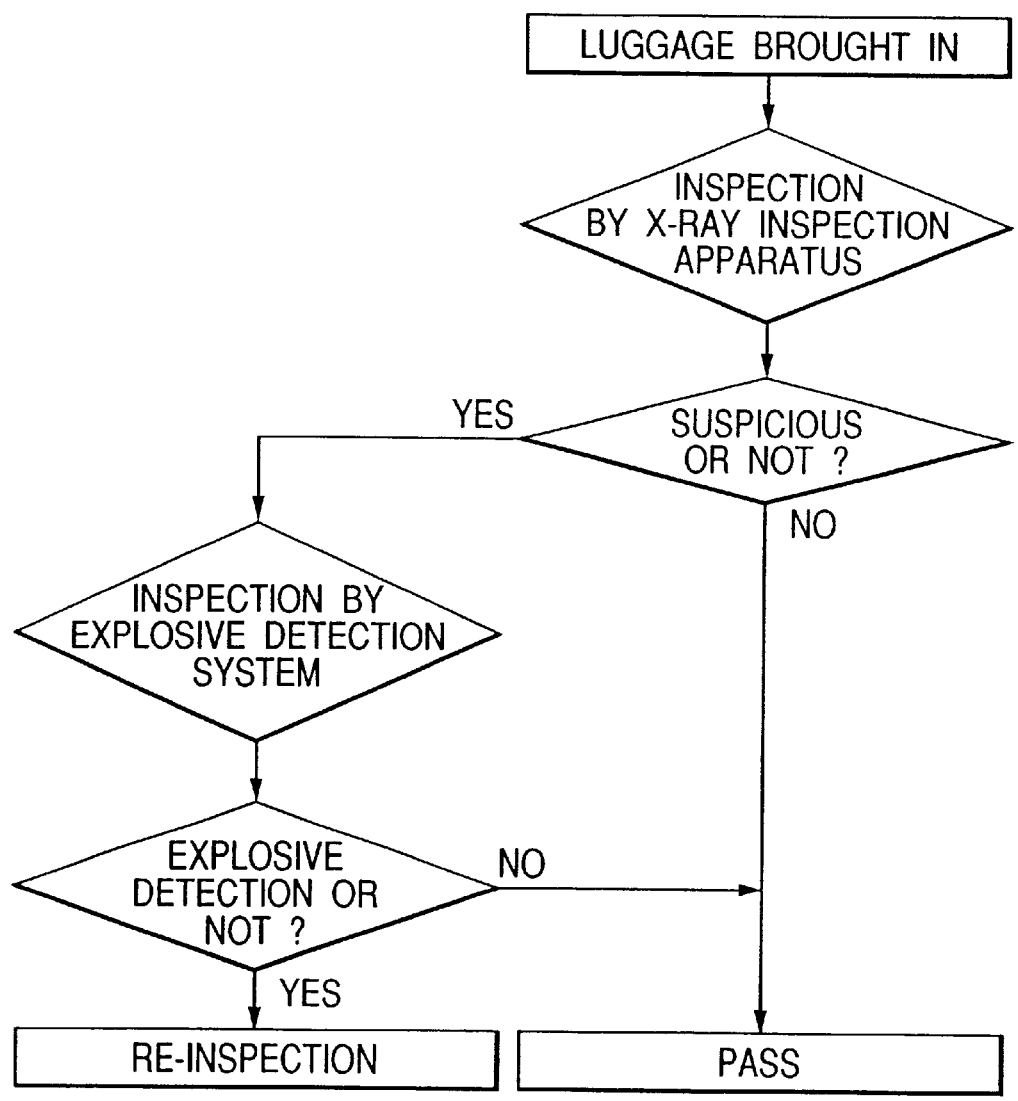
FIG. 26 is a flowchart of an operation of an off-line explosive detection system combined with an X-ray inspection system.

A flowchart for such an inspection as described above is shown in FIG. 26. When no abnormality is detected by the X-ray inspection system 3a and the explosive detection system 4 for off-line analysis, the luggage is permitted to pass. When an abnormality is detected, a close reinspection is made. In FIG. 1, the X-ray inspection system 3a is used together with the explosive detection system 4 for off-line analysis, but it is possible to use only the explosive detection system 4 for off-line analysis. The object to be inspected also may pass through the X-ray inspection apparatus after being subjected to inspection by the explosive detection system 4 for off-line analysis. In this case, when there is an explosive, the time for the inspection by the X-ray inspection apparatus 3 is eliminated. Thus, it is possible to perform an inspection using only the explosive detection system 4 for off-line analysis. This situation is effective for the case in which an object which is sensitized, discolored or deformed by X-rays is stored inside the luggage.

Such an explosive detection system 4 for off-line analysis may be applied to a vehicle inspection for determining whether or not there is an explosive in the trunk of the vehicle.

Such an inspection system has the following advantages. If an explosive, such as a plastic bomb, exists as a thick lump inside luggage, it may be detected by an X-ray inspection apparatus. However, if such an explosive exists in the form of a thin sheet, X-rays are substantially transmitted through it. Thus, the explosive is difficult to detect. In this case, if in the next stage the inspector inspects the luggage by using the explosive detection system for off-line analysis, even an explosive in sheet form can be detected in the case where vapor of the explosive leaks inside of the luggage or outside of the luggage. Thus, the possibility that the explosive can be detected is made higher than in the case of using only the X-ray inspection system. In the reinspection, whether a substance inside the luggage is an explosive or not can be checked on the spot of the analysis from vapor of the substance. Moreover, the kind of substance can be also analyzed. This case is more useful than the case of using the X-ray inspection system alone.

The action of the actual analyzing region will be described hereinafter, referring mainly to FIG. 7. A gas sample, which is an object to be inspected, is introduced from a gas sample introduction port 17 in a gas sample introduction probe.

Figure 9:
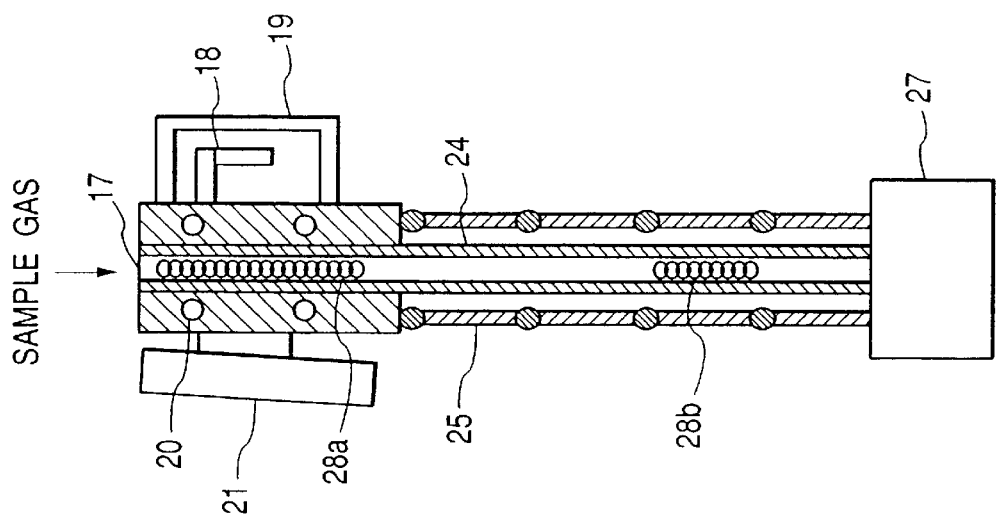
FIG. 9 is a partial sectional view of a system of the present invention.
Figure 10:
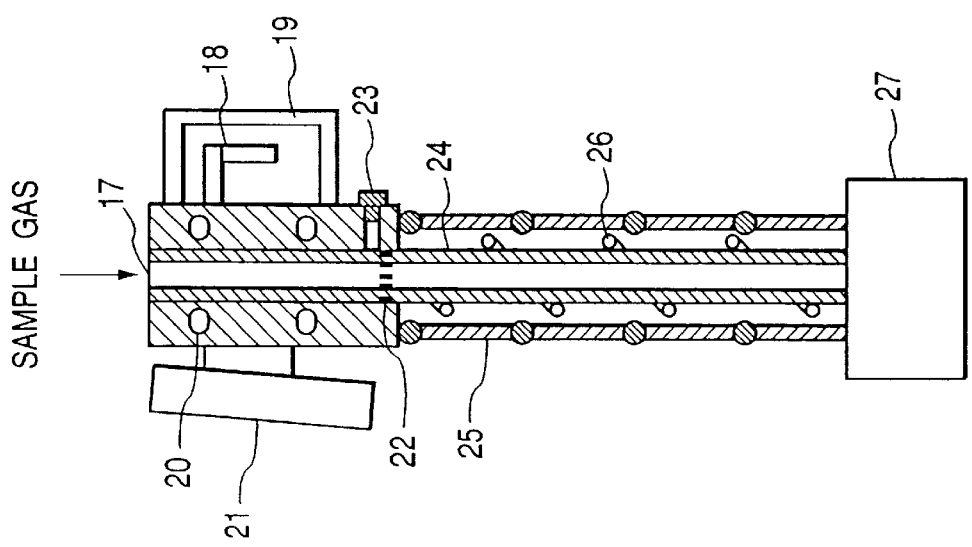
FIG. 10 is a partial sectional view of a system of the present invention.

The details of the gas sample introduction probe are illustrated in FIGS. 9 and 10. The case illustrated in FIG. 9 will be explained first. A gas sample introduction pump 27 is necessary for introducing a gas sample from the gas sample introduction port 17. As this gas sample introduction pump 27, there is used a gas introduction pump having a mechanical mechanism, such as a diaphragm pump. The flow amount of the introduced gas sample is about from several liters to several tens of liters per minute. The capability of the used gas sample introduction pump 27 depends greatly on the length of a gas sample introduction pipe 24. If the gas sample introduction pipe 24 becomes longer, it is necessary to use a gas sample introduction pump 27 having a higher capability. In order to prevent the sample gas from being absorbed onto the inner wall of the gas sample introduction pipe 24, it is necessary to raise the temperature inside this pipe 24 at the time of introducing the gas sample. As the gas sample introduction pipe 24, a flexible pipe is used. A pipe 25 which is hard but can be bent, such as a pipe in the form of a bellows, is arranged around the gas sample introduction pipe 24 to reinforce the pipe 24 structurally. In order to prevent the sample gas from being absorbed onto the inner wall of the pipe 24, a heater 26 for the pipe 24 is wound around the pipe 24 to control the temperature thereof. This temperature is usually set up to room temperature (10–30° C.) or higher. The highest temperature is about 200° C. On the other hand, in the case where the gas sample introduction pump 27 is used to introduce the gas sample, a handle 19 is fixed onto the tip of a probe to make it convenient to hold the probe and a switch 18 of the gas sample introduction pump 27 is disposed near the handle 19. It is also an important point that the probe tip heater 20 is disposed at the probe tip to prevent absorption of the gas sample at the probe tip, or a filter 22 is disposed so as not to suck large particles or rubbish directly toward the gas sample introduction pipe 24. In this case, a clean-out port 23 for cleaning the inside of the filter periodically is preferably provided in such a manner that particles stopped up in the filter 22 can easily be taken out. In the case where the target is a solid sample, a solid sample heating means 21 such as an infrared ray lamp or a halogen lamp may be provided since heating of the solid sample causes more vapor to be generated and detection is also made easier. In the case where the solid sample is sampled, it is also an important point at the time of using the present system that the solid sample is heated by means of this solid sample heating means.

Incidentally, in the case where the length of the gas sample introduction pipe 24 is over several meters, if the present system is made up as a structure as shown in FIG. 9, it becomes necessary for the wound heater 26 for the pipe 24 to be lengthened accordingly. Thus, costs for the production of the probe rise. In order to overcome this drawback, the following structure may be adopted. That is, as illustrated in FIG. 10, it is preferable to dispose a metal wire heater 28a in a coil form, for heating the gas sample which passes by selectively supplying electricity thereto. In the case such where plural heaters are disposed at constant intervals, a structure may be adopted in which the heater 28a is disposed and additionally a heater 28b is disposed on the passage of the sample introduction pipe 24, as shown in FIG. 10. In the case where the gas sample introduction pipe 24 is long, the number of such heaters may be increased. In an actual operation of the system, suction of the gas sample is started by the gas sample introduction pump 27 and subsequently heating of the metal wire heaters 28a and 28b is begun by turning on electricity to the heater. After a certain time, at which the metal wire heaters 28a and 28b are sufficiently heated, an inspection is started. Such a sequence makes it possible to relieve problems, such as a problem that the sample gas having a low temperature is introduced into the gas sample introduction pipe and is then absorbed. By adopting such a structure, it is sufficient if the metal wire heaters 28a and 28b are arranged at regular intervals even when the gas sample introduction pipe 24 is long. When heating by turning on electricity to the heater is used, the temperature of the metal wire heater rises to a given temperature for several seconds. Thus, it is unnecessary to heat this metal wire heater at all times, thereby producing an advantage that not only costs for the production but also costs for the operation can be lowered.

In order to prevent large particles, including a water drop, from being introduced, it is preferable that the metal wire heater 28a is positioned at the tip of the gas sample introduction pipe 24. In the case where the metal wire heater heated at a high temperature is positioned immediately adjacent the gas sample introduction port 17, the following possibility rises: particles, including a water drop, are heated and vaporized. Of course, as illustrated in FIG. 9, the filter 22 or the clean-out port 23 may be set up at the back thereof.

Figure 8:
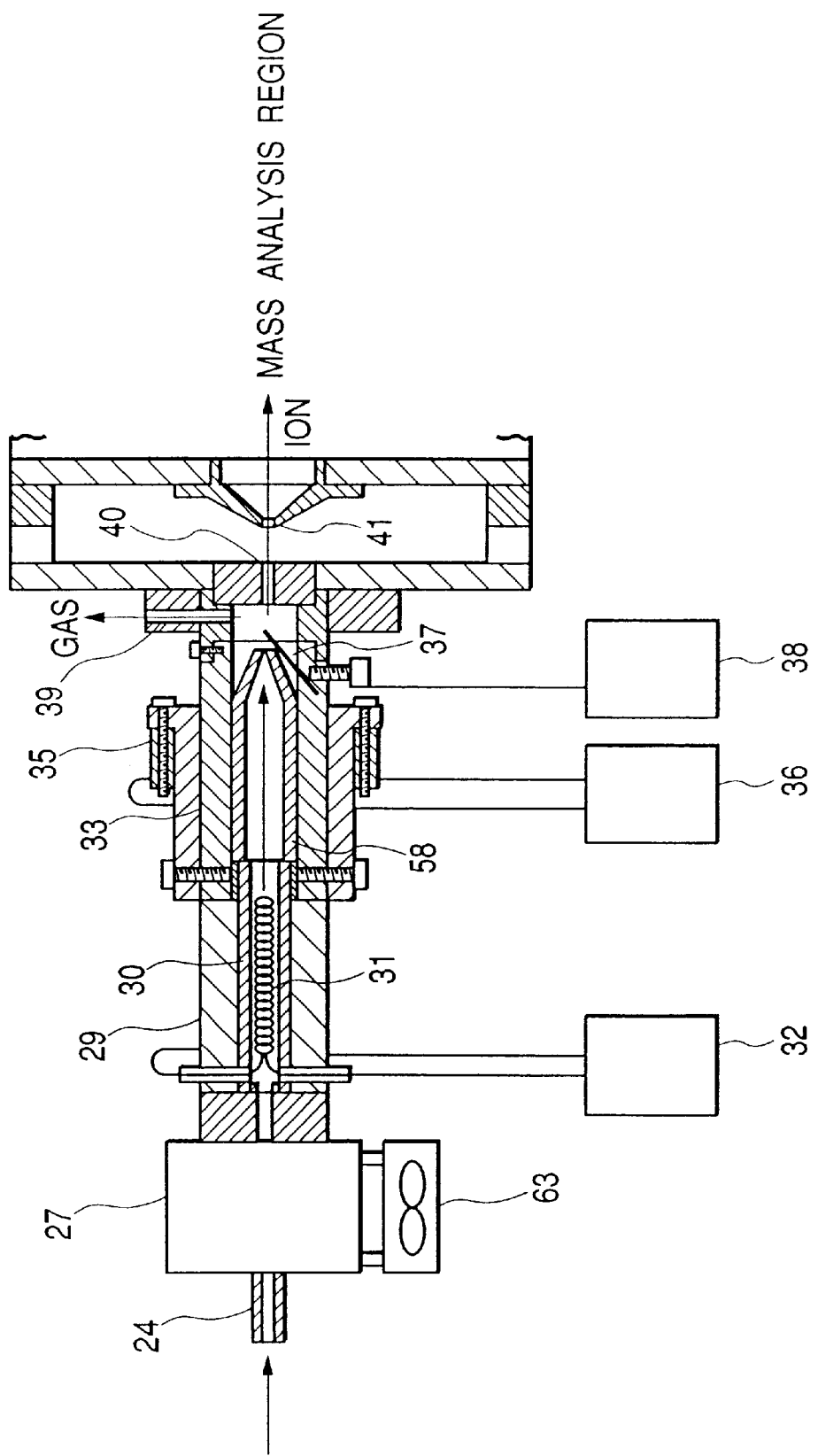
FIG. 8 is a partial sectional view of a system of the present invention.

As illustrated in FIG. 8, the sample gas which is forcibly introduced into the gas sample introduction pipe 24 by the gas sample introduction pump 27 is first introduced into a gas sample heating furnace 29. In this case, if the gas sample introduction pump 27 is continuously operated, a pump cooling fan 63 may be used to cool the driving unit of the pump 27. In this gas sample heating furnace 29, a metal wire heater 31 for heating a gas sample, inside an insulating pipe 30 made of a material resisting high temperature, such as quartz, disposed in blocks made of a metal, is heated by turning on electricity to the heater to heat the gas sample passing this region. As the metal wire heater 31, a wire made of a metal, such as Nichrome wire, in a coil form is used. The diameter of the insulating pipe depends on the flow amount of the gas, but the diameter is about 5 mm in the case where the gas is introduced in a flow amount of 2 liters per minute. The length of the insulating pipe is about 10 cm. The heating temperature of the metal wire heater 31 depends on the sample to be inspected but is about 30–400° C. It is important that the introduced gas sample does not advance directly to a corona discharge region as described later. This is because corona discharge becomes unstable when particles (including water drops) are directly introduced into the corona discharge region. In the case where a heating region for the gas sample, such as the metal wire heater 31 for heating the gas sample as shown in FIG. 8, is in the front of the corona discharge region, even if particles are introduced, they collide with the heater 31, which is heated to a high temperature, and then are vaporized in this region. The temperature of this heater 31 is controlled by a heating source 32 for the metal wire heater 31. Usually, the temperature of this region is kept at about 50–400° C. The gas sample heating furnace 29 may be unnecessary if the gas sample is sufficiently heated at the gas sample introduction pipe 24, which is a region prior to the furnace 29.

The gas sample which has passed through the sample heating furnace 29 is introduced into the corona discharge region for ionizing the gas. The tip of a gas sample introduction path 58 with a choke is positioned near a needle electrode 37 for corona discharge so that the introduced gas sample is effectively forwarded to the corona discharge region around the tip of the needle electrode 37 for corona discharge. In the case where the inner diameter of the path is about 5 mm, if the inner diameter of its tip is made up to about 1 mm, the introduced gas sample is certainly and effectively introduced into the corona discharge region around the tip of the needle electrode 37 for corona discharge. In this case, the length of the gas sample introduction path 58 is about 5 cm.

The gas sample introduction path 58 near the needle electrode 37 for corona discharge is made of an insulating material, such as Teflon, glass ceramic, ceramic or the like, so as not to weaken the electric field around the tip of the needle electrode 37. This region, as well as the gas sample heating furnace 29, can be heated by a heater 35 for the corona discharge region. The temperature of this region is usually kept at 50–300° C. by a power source 36 of the heater for heating the corona discharge region.

The needle electrode 37 for corona discharge is set up in the corona discharge region 33 so that a high negative voltage (about from −2 to −5 kV) can be applied by a power source 38 for corona discharge. In this case, the distance between the needle electrode 37 and an opposite electrode 33 around it is from about 1 to 10 mm. A surplus gas, other than the ions and molecules introduced through a first aperture 40, is discharged through a surplus gas exit port 39 out of the system.

Figure 7:
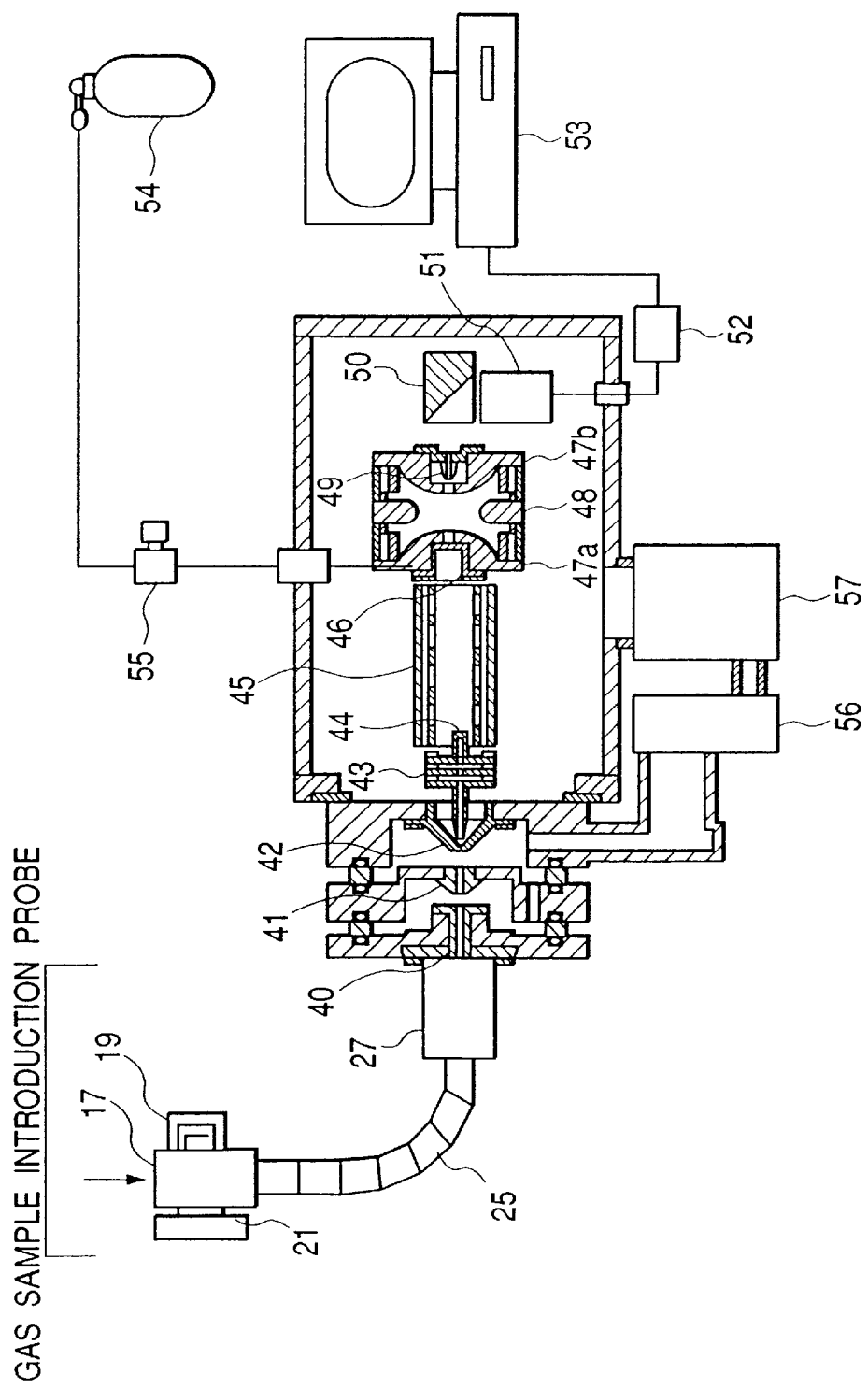
FIG. 7 is a partial sectional view of a system of the present invention.

In order to analyze ions generated in the corona discharge region, various kinds of mass spectrometers can be used, but the following will describe a case of using an ion trap mass spectrometer, which is an ion storing type device, with reference to FIG. 7. The following description can be applied as well to cases of using other types of mass spectrometers, such as a quadrupole mass spectrometer and a magnetic sector type mass spectrometer. As regards the ions generated in the corona discharge region, cluster ions are dissociated by heating and collosion with neutral molecules, so as to generate ions of the sample molecules, in the step in which the ions pass through the first aperture 40 (diameter: about 0.3 mm, length: about 20 mm), a second aperture (diameter: about 0.2 mm, length: about 0.5 mm) and a third aperture (diameter: about 0.3 mm, length: about 0.5 mm) of a differential pumping region heated by the heater. A voltage can applied between the first aperture 40 and the second aperture 41 and between the second aperture 41 and the third aperture 42, so that the ion transmission efficiency is improved and simultaneously the cluster is dissociated by the collision with remaining molecules. The differential pumping region is usually evacuated by a roughing vacuum pump 56, such as a rotary pump, a scroll pump, or a mechanical booster pump. A turbo-molecular pump may be used in order to evacuate this region. The pressure between the second aperture 41 and the third aperture 42 is between 0.1 and 10 Torr. The generated ions pass through the third aperture 42 and subsequently are focused by an electrostatic lens 43. As this electrostatic lens 43, an einzel lens composed of three electrodes, or the like is usually used. After the ions pass through a slit 44, the ions are deflected through a deflector 45 and then are introduced, through a gate electrode 46, into an ion trap mass spectrometer comprising a pair of bowl-like endcap electrodes 47a and 47b and a ring electrode 48. The slit 44 restricts a three-dimensional angle of a jet, including neutral particles, flowing-in from a skimmer and prevents surplus particles and the like from being introduced into the ion trap mass spectrometer. The deflector 45 is used to indirectly introduce the neutral particles which have passed through the skimmer into the ion trap mass analyzing region through an aperture of the endcap electrode 47a. In this embodiment, the deflector 45 is a double cylinder type deflector which comprises an inner cylinder having many openings and an outer cylinder. Deflection is attained by using an electric field spread out from the openings of the inner cylinder. The gate electrode 46 fulfils a function whereby ions are not introduced from the outside to the mass analyzing region when the ions trapped in the ion trap mass analyzing region are taken out of the system. The ions introduced into this ion trap mass an analyzing region collide with a gas, such as helium, introduced into the ion trap mass analyzing region, so that their orbit is made smaller. Subsequently, the ions are discharged out of the system by scanning a high frequency electric field applied to the ring electrode 48, they pass through a pulling-out lens 49, and are then detected by an ion detector. A gas such as helium is supplied from a supplying source such as a cylinder 54 through a regulator 55. One of the merits of the ion trap mass spectrometer is that since this spectrometer has a property of accumulating ions, ions can be detected by extending the time for accumulating the ions even when the concentration of the sample is thin. Therefore, even when the concentration of the sample is low, the ions can be highly concentrated at the ion trap mass analyzing region. Thus, pre-treatment of the sample can be made very simple. When the ions taken-out from the ion trap mass analyzing region are detected, the ions are converted into electrons by a conversion diode 50 and then the electrons are detected by a scintillation counter 51. The resultant signals are amplified by an amplifier 52 and then are forwarded to a data processing system 53.

A chamber, including the electrostatic lens 43, the slit 44, the deflector 45, the gate electrode 46, the ion trap mass analyzing region and the ion detector, is evacuated by the turbo-molecular pump 57. An auxiliary pump is necessary at the backpressure side of the turbo-molecular pump 57. This can also be used as the roughing vacuum pump 56, which is used in the differential pumping region. In this embodiment, a scroll pump having a pumping speed of about 900 liters per minute is used at the differential pumping region and a turbo-molecular pump having a pumping speed of about 200 liters per second is used as the pumping device for the chamber. The scroll pump is also used as the auxiliary pump of this turbo-molecular pump. Such a system simplifies the pumping system of the atmosphere ionizing mass spectrometer, which is liable to be complicated. In the present system, the deflector 45 is used, but there are naturally cases in which ions are not deflected. In such cases, the ion trap mass analyzing region is arranged just after the electrostatic lens 43. In the embodiment illustrated in FIG. 7, the two-stage differential pumping system is used, but a three or more stage differential pumping system may be used. In this case, it is permissible that the number of the apertures used for differential pumping at the first stage is reduced from 3 to 2 and the number of differential pumping stages is increased at the high vacuum side, which involves the second stage and the subsequent stages.

Figure 25:
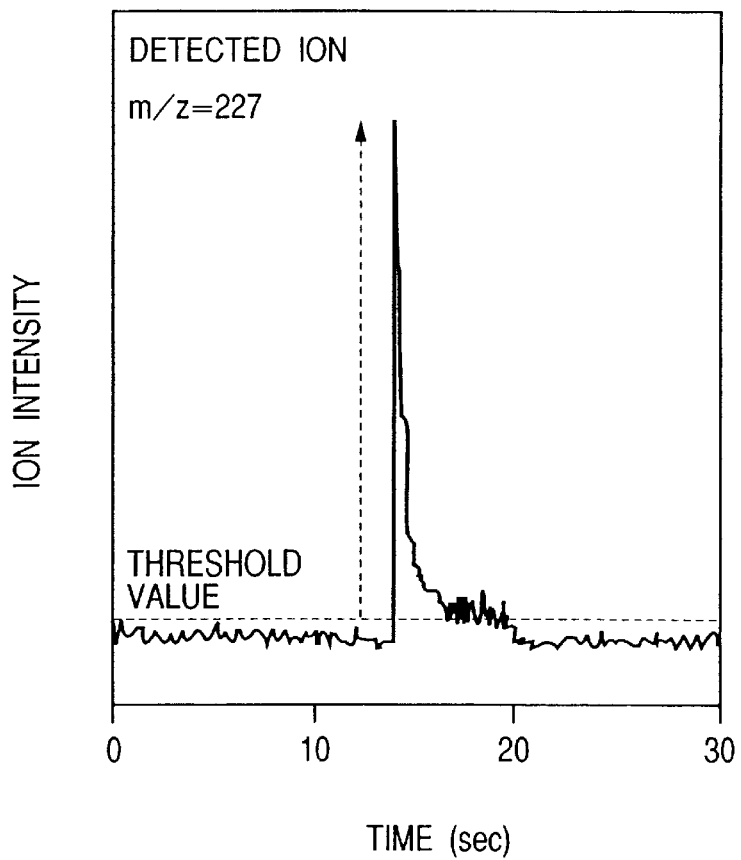
FIG. 25 is a diagram showing a detecting scheme in an explosive detection system.

The data processing system 53 usually displays the relationship between mass to charge ratios and ion intensity (mass spectrum), the change with the passage of time in ion intensity of a certain mass to charge ratio (mass chromatogram), and the like. As described above, the final display in the data processing system 53 may be not only a mass spectrum and a mass chromatogram, but also those further simplified displays. In other words, in the case of an explosive detection system, it is sufficient to merely display whether a nitrocompound which is brought into question is detected or not. In order to specify an owner of luggage, the owner's name is displayed on a passenger-researching screen from a code read in a non-illustrated bar coder so that the owner can be quickly specified. As shown in, for example, FIG. 25, concerning a certain ion to be detected (TNT in this case. The detected ion is a negative ion in which an electron is attached to a TNT molecule. Its mass is 227.), a threshold is set up to a certain noise level. When a signal over the level is detected, this ion is regarded as being detected. At this time, in order to distinguish the signal from mere spike noises, an algorithm is used such that if the signal over the above-mentioned level is being observed over some time, for example, such a signal is integrated during a period from 1 to 5 seconds, this signal is regarded as a signal indicating that the ion is detected. Error operation can be reduced by adding such an algorithm. This approach can sufficiently cope with the requirement that detection should be performed as quickly as possible when luggage is inspected. In this case, the final display may be a display as shown in FIG. 24. An indicating device 64 has an indicator 65 for a substance corresponding to an ion to be detected. When for example, substance "A" is detected, the indicator "A" is turned on and off according to the above-mentioned algorithm, thereby indicating that substance "A" is detected. In this case, it is permissible to simultaneously provide an indicator 66 and an alarm 67 for indicating the degree of concentration being detected. (As simple information, information as to whether the amount is large or small is permissible.)

Figure 14:
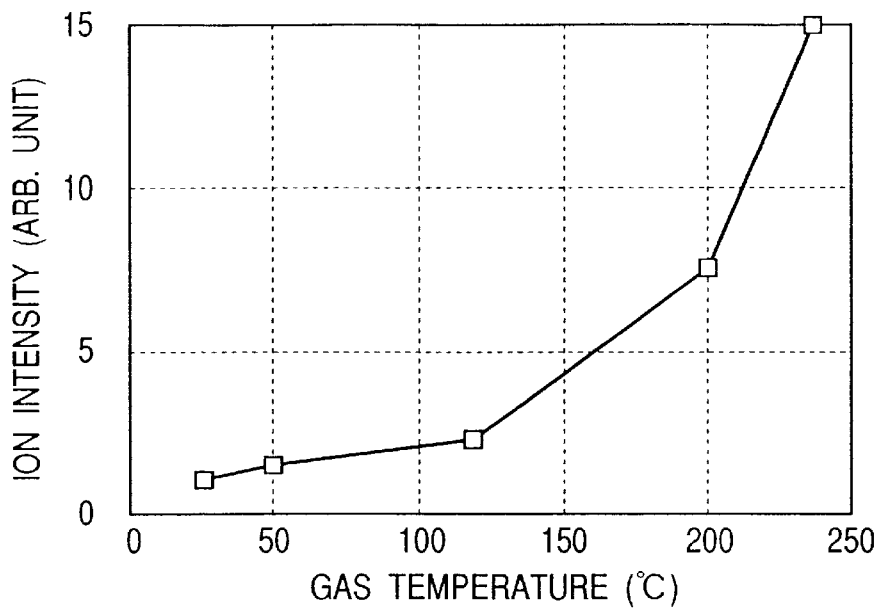
FIG. 14 is a graph showing the relationship between gas temperature and ion intensity.
Figure 15:
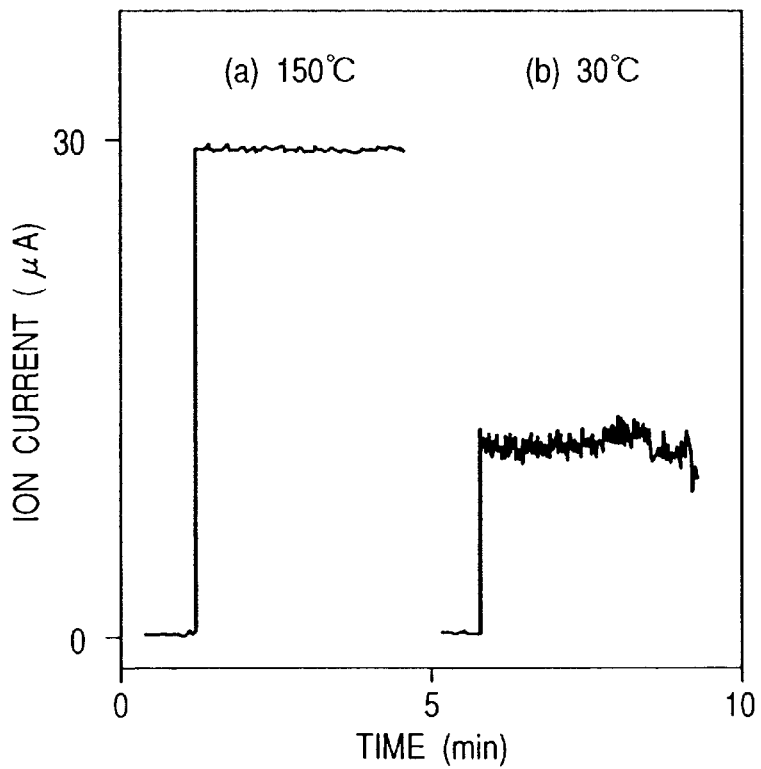
FIG. 15 is a graph showing the difference between the ion intensity in the case where gas is heated and that in the case that gas is not heated.

The importance of the gas sample heating furnace 29, as described above, can also be understood from data shown in FIGS. 14 and 15. FIG. 14 shows the relationship between the temperature of a gas sample and the ion intensity, which was obtained when the gas sample is heated by the gas sample heating furnace 29. It can be understood that as the gas temperature rises, the ion intensity rises abruptly. A remarkable change was observed, in particular, over 100° C. FIG. 15 shows the difference between ion intensities obtained in the cases where the temperature of the gas sample is (a) 150° C. and (b) 30° C. The sample being used was mononitrotoluene. Peaks were obtained by sucking vapor from the sample at room temperature by means of the gas sample introduction pump 27. It can be understood that when the same corona discharge voltage (=2.5 kV) was used, the electric current in the case in which heating was performed was 2.5 times as much as that in the case where heating was not performed. Moreover, the stability of the electric current in the former case was far better than that in the latter case. If the temperature of the gas sample rises to a high temperature, for example, 100° C. or higher, water contained in the introduced gas sample is also vaporized so that ionizing by corona discharge is effectively and stably conducted. If the temperature of the needle electrode 21 for corona discharge is indirectly raised by the gas sample heated to a high temperature, a high corona discharge current can be obtained even when the same discharge voltage is applied. Therefore, the ionization efficiency is also raised.

Figure 13A:
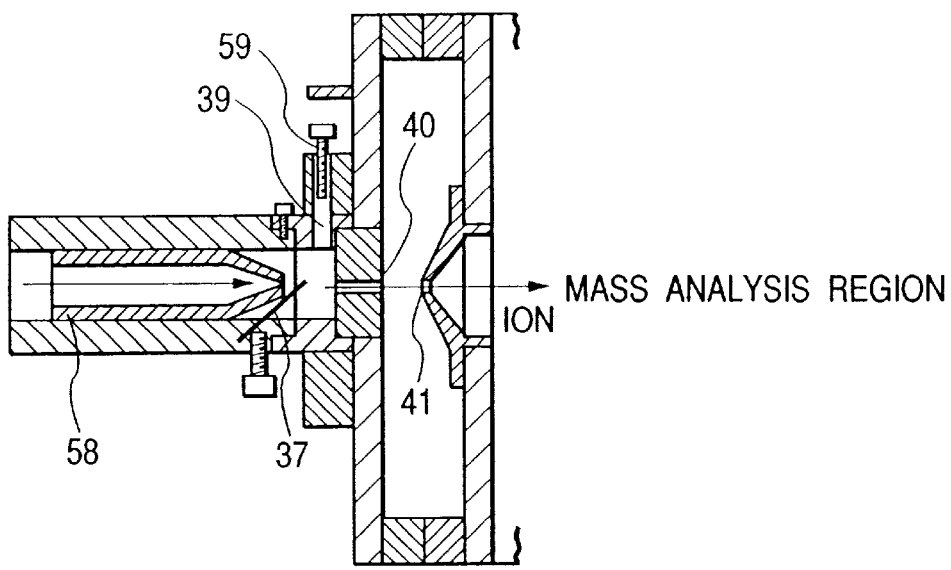
FIG. 13A is a sectional view of a pressure adjusting mechanism.
Figure 13B:
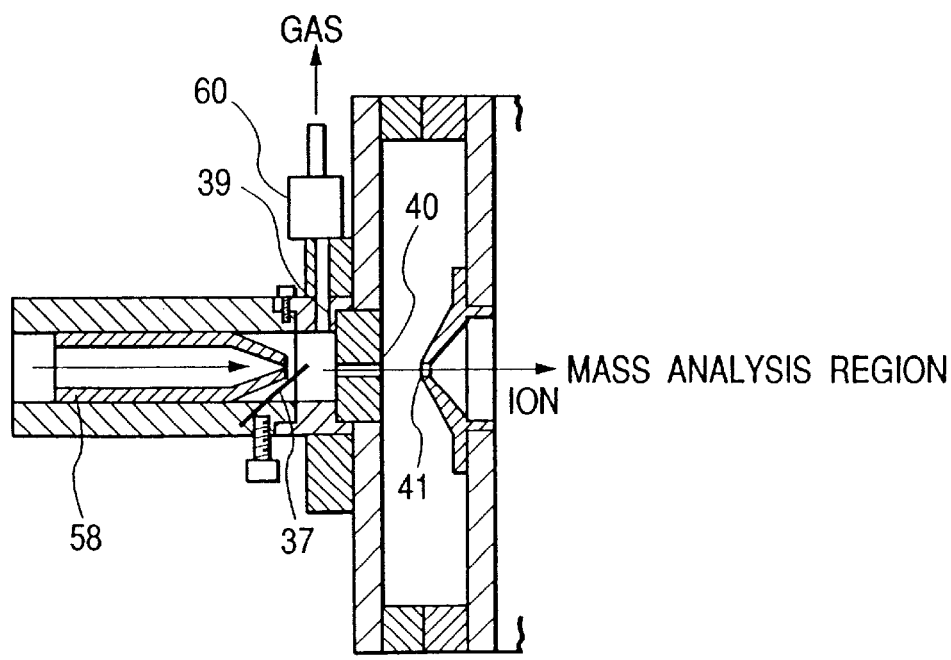
FIG. 13B is a sectional view of a pressure adjusting mechanism.
Figure 16:
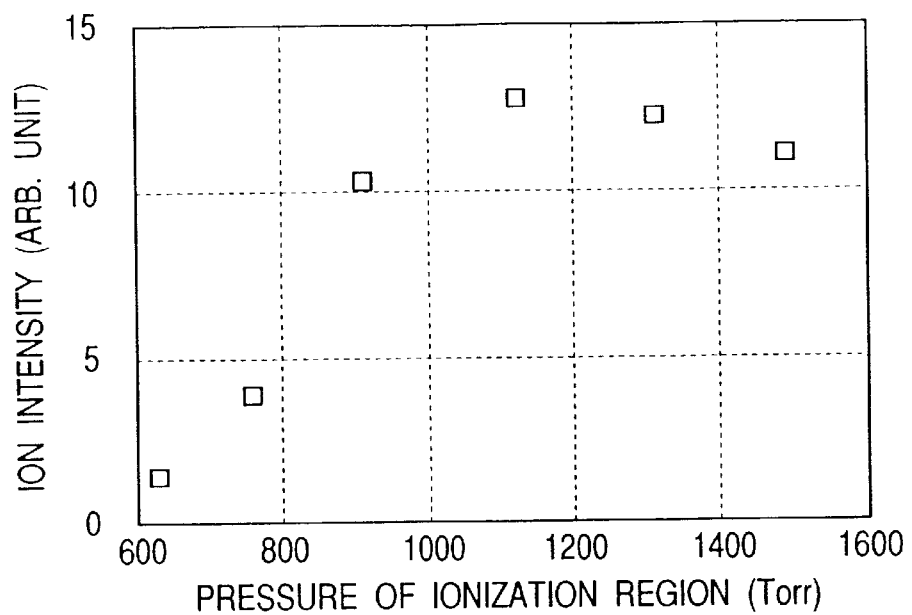
FIG. 16 is a graph showing the relationship between pressure in the ionization region and ion intensity.
Figure 17:
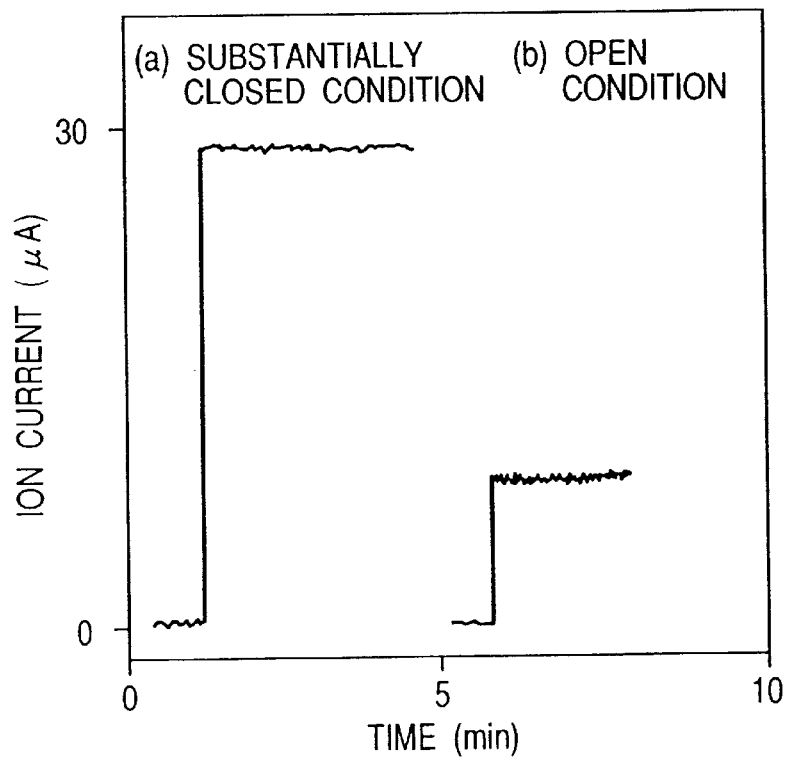
FIG. 17 is a graph showing the difference between the ion intensity in the case where the ionization region is closed and that in the case where the ionization region is open.

The pressure in the region where ions are generated by corona discharge is also important. An atmospheric pressure chemical ionization region using corona discharge generally has the surplus gas exit 39 for taking surplus gas which does not flow through apertures for taking ions in a vacuum out of the ionization region. Accordingly, this surplus gas exit 39 is always open. The corona discharge region is substantially set up to atmospheric pressure (760 Torr). In reality, however, as the density of molecules in the corona discharge region is higher, the ionization efficiency is higher. Thus, the optimal pressure in the corona discharge region is higher than 760 Torr, which is atmospheric pressure. On the other hand, if the pressure around the aperture (diameter: about 0.2–0.5 mm) for taking ions in a vacuum is too high, the number of molecules flowing through the aperture into the mass analyzing region under a high vacuum becomes too large. Thus, it is difficult to maintain a high vacuum in the mass analyzing region. As shown in FIGS. 13A and 13B, therefore, the surplus gas exit 39 is shut, and gas is continuously introduced by the gas sample introduction pump 27 to heighten the pressure in the corona discharge region. In this case, a structure shown in FIG. 13A or 13B is adopted. In FIG. 13A, a weight 59, which is made of a light material, for lowering the conductance of the surplus gas exit, is put in the exit, and the pressure in the corona discharge region is controlled. If the pressure in the corona discharge region becomes too high, the weight 59 floats so that the surplus gas is discharged from the surplus gas exit. On the basis of the relationship between the flow amount of the gas flowing into the corona discharge region and the weight, the pressure in the corona discharge region can be controlled to or near an optimal value. As shown in FIG. 13B, a pressure adjusting region 60 is arranged at the surplus gas exit, and the pressure in the corona discharge region can be controlled by this pressure adjusting region 60 during the operation of the gas sample introduction pump 27. FIG. 16 shows the relationship between pressure of the ionization region and ion intensity. It is clear that the maximum value of the ion intensity is above 760 Torr. FIG. 17 shows the comparison of the sensitivity measured in the case where a weight was put in the surplus gas exit to raise the pressure (to about 1.2 atom.) in the corona discharge region and that measured in the case where the surplus gas exit was opened to set the pressure to substantially atmospheric pressure (1 atom.). The sample being used was mononitrotoluene. Peaks were obtained by sucking vapor from the sample at room temperature by means of the gas sample introduction pump 27. The sensitivity of the former case was about 3 times as much as that in the latter case. Thus, it can be understood that it is effective to raise the pressure in the corona discharge region.

Figure 11:
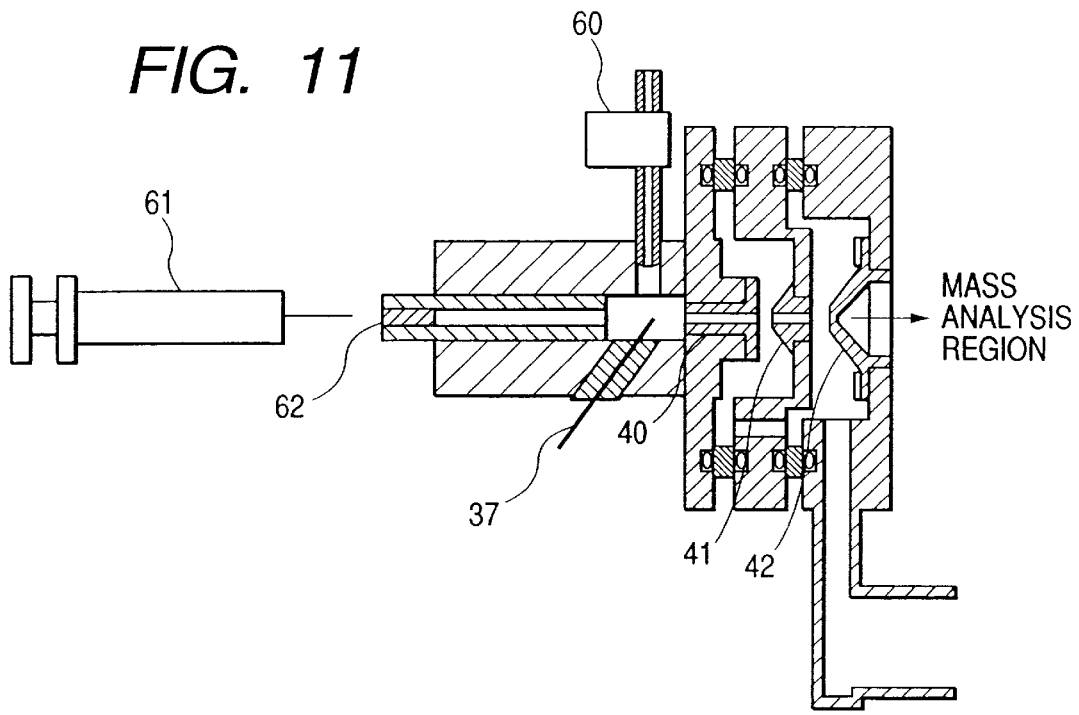
FIG. 11 is a partial sectional view of a system in a syringe introduction mode.
Figure 12:
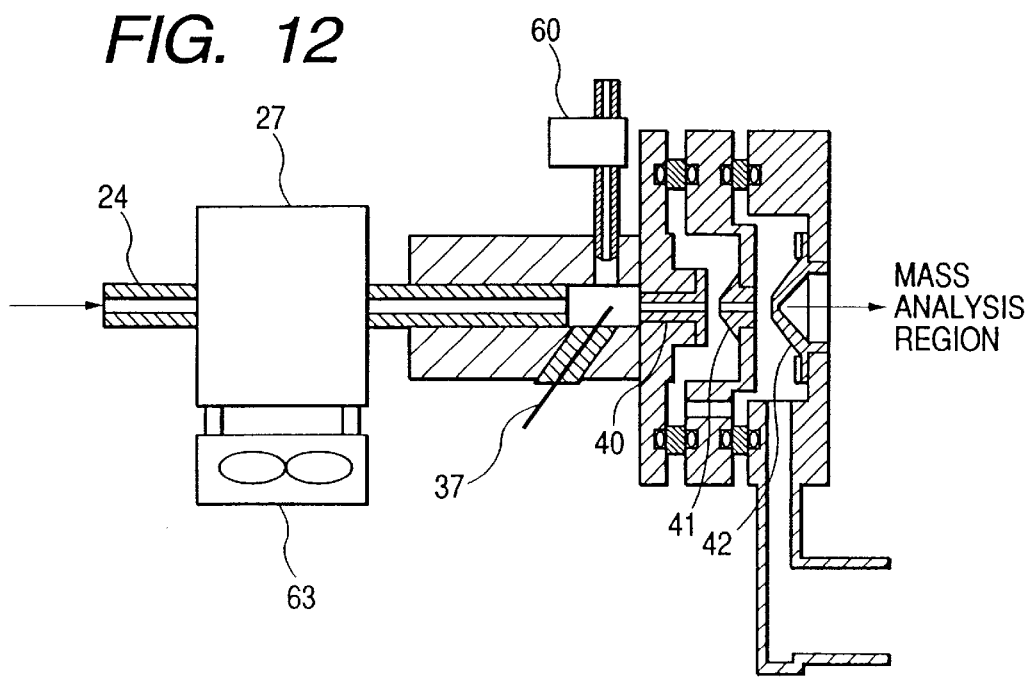
FIG. 12 is a partial sectional view of a system in a continues introduction mode.
Figure 18:
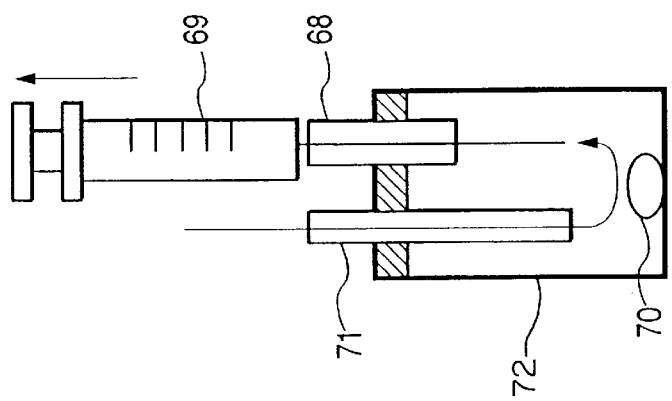
FIG. 18 is a diagrammatic view showing a manner for sampling a sample vapor in a syringe introduction mode.
Figure 21:
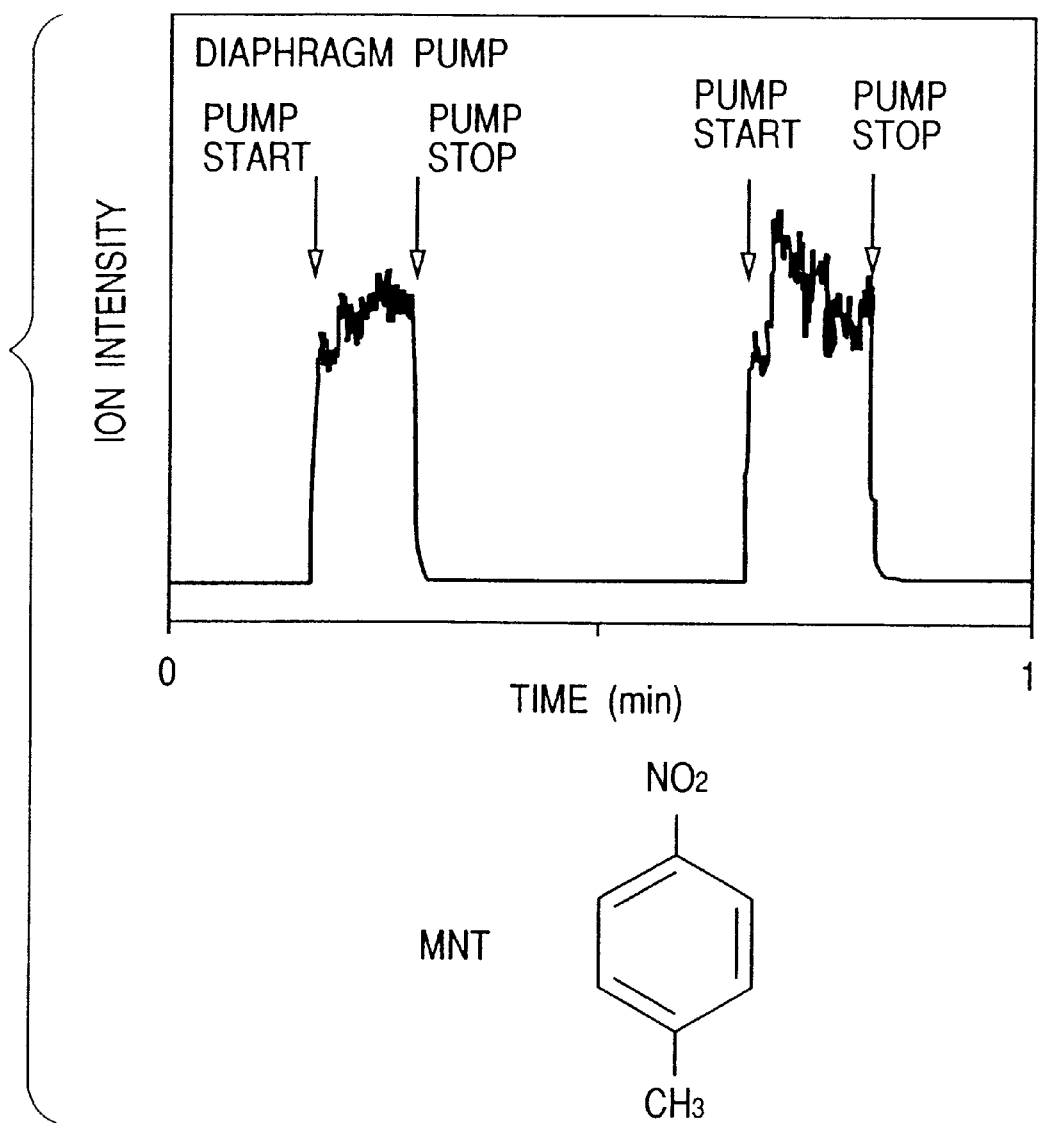
FIG. 21 is a diagram showing the chemical formula of MNT and an example of the results of detection of MNT vapor in a continuous introduction mode.

The case in which a gas sample is continuously introduced by the gas sample introduction pump 27 to make an inspection, as shown in FIG. 12, has been described above. In this case, such a result as shown in FIG. 21 is obtained (sample: mononitrotoluene (MNT). On the other hand, it is possible for a gas sample to be collected in a syringe 61 and then is directly and off-line introduced into the system through a receptor 62, as shown in FIG. 11. In this case, such a sampling approach as shown in FIG. 18 may be used. That is, a solid sample 70 is put in a sample bottle 72, and a syringe 69 is used to sample vapor of the solid sample 70 from a gas sample introduction port 68. In the case that the solid sample is powdery, an air intake port 71 is disposed at the bottle so as not to blow up powder from the solid sample. Under such conditions, the syringe is used to collect several tens of cubic centimeters of air including vapor of the solid sample. The air is directly introduced into the spectrometer, in the manner shown FIG. 11.

Figure 19:
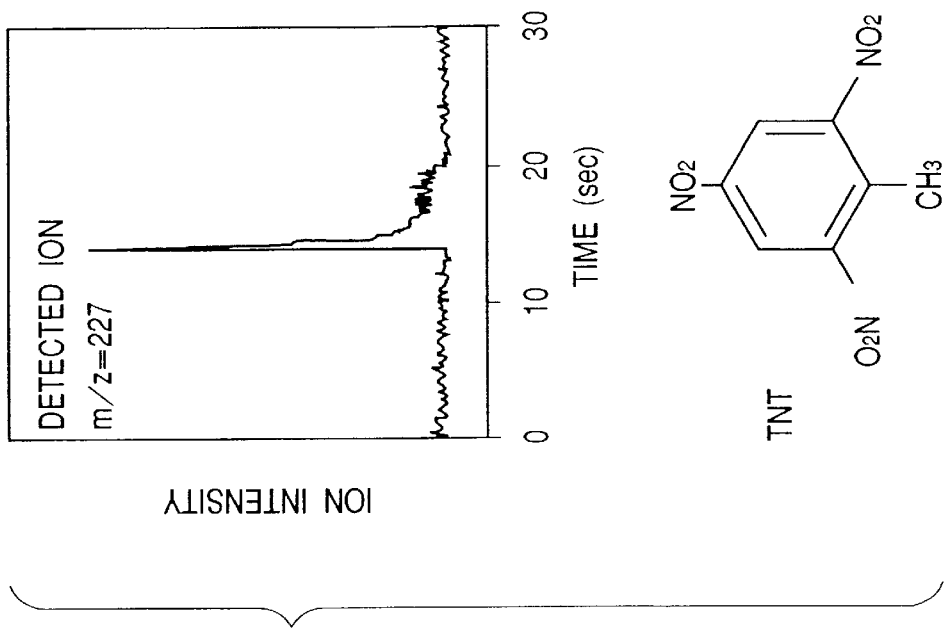
FIG. 19 is a diagram showing the chemical formula of TNT and an example of the results of detection of TNT vapor in a syringe introduction mode.
Figure 20:
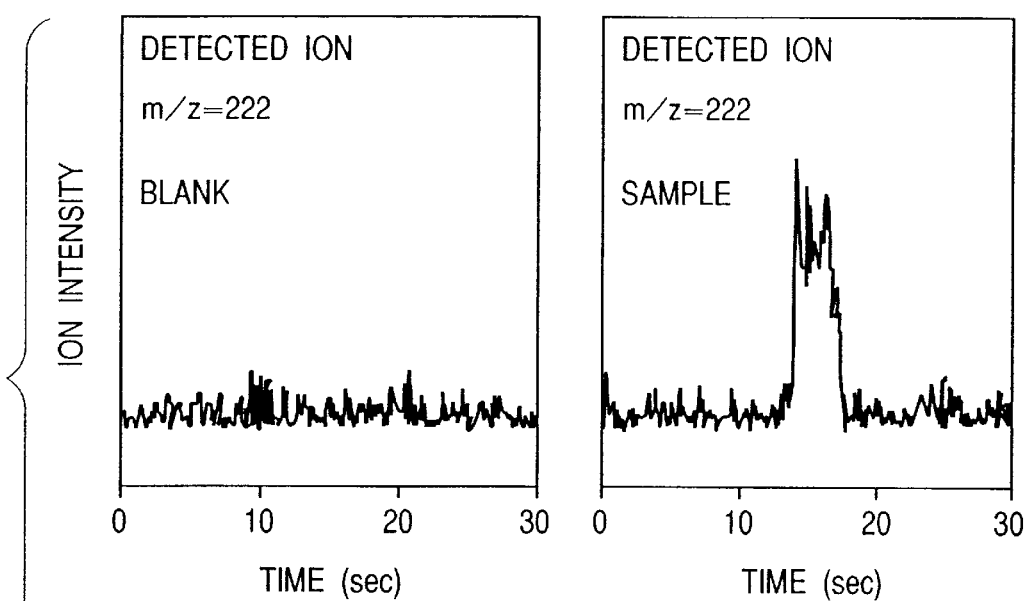
FIG. 20 is a diagram showing the chemical formula of RDX and an example of the results of detection of RDX vapor in a syringe introduction mode.
Figure 20:
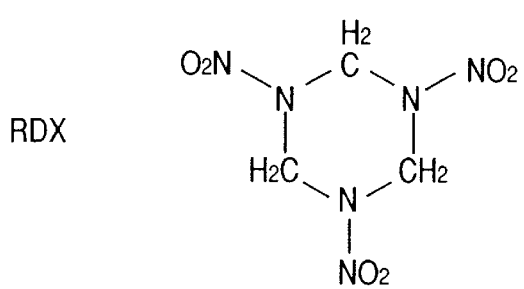

If the spectrometer as described above is used, nitrocompounds having a low vapor pressure can be detected with high sensitivity. This is because the negative ionization efficiency of the compounds by negative corona discharge is high. Concerning nitrocompounds, their negative ionization efficiency tends to be higher with the increase in the number of their nitro groups. Even substances having a low vapor pressure can be sufficiently detected, such as trinitrotoluene (TNT) as shown in FIG. 19, and RDX as shown in FIG. 20. In such detection, the syringe introduction mode shown in FIG. 11 is used. Of course, if the method of the present invention is used, it is possible to detect even nitrocompounds having a single nitro group (such as mononitrotoluene) or even those having two nitro groups (such as dinitrotoluene) with a high sensitivity.

Figure 22:
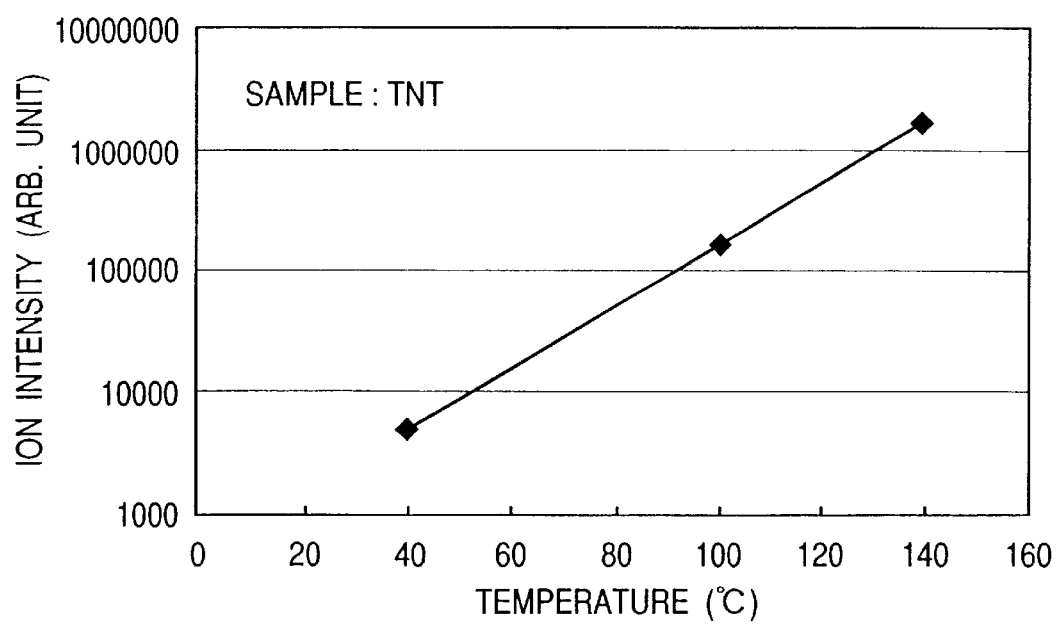
FIG. 22 is a graph showing the relationship between temperature of the TNT sample and ion intensity.
Figure 23:
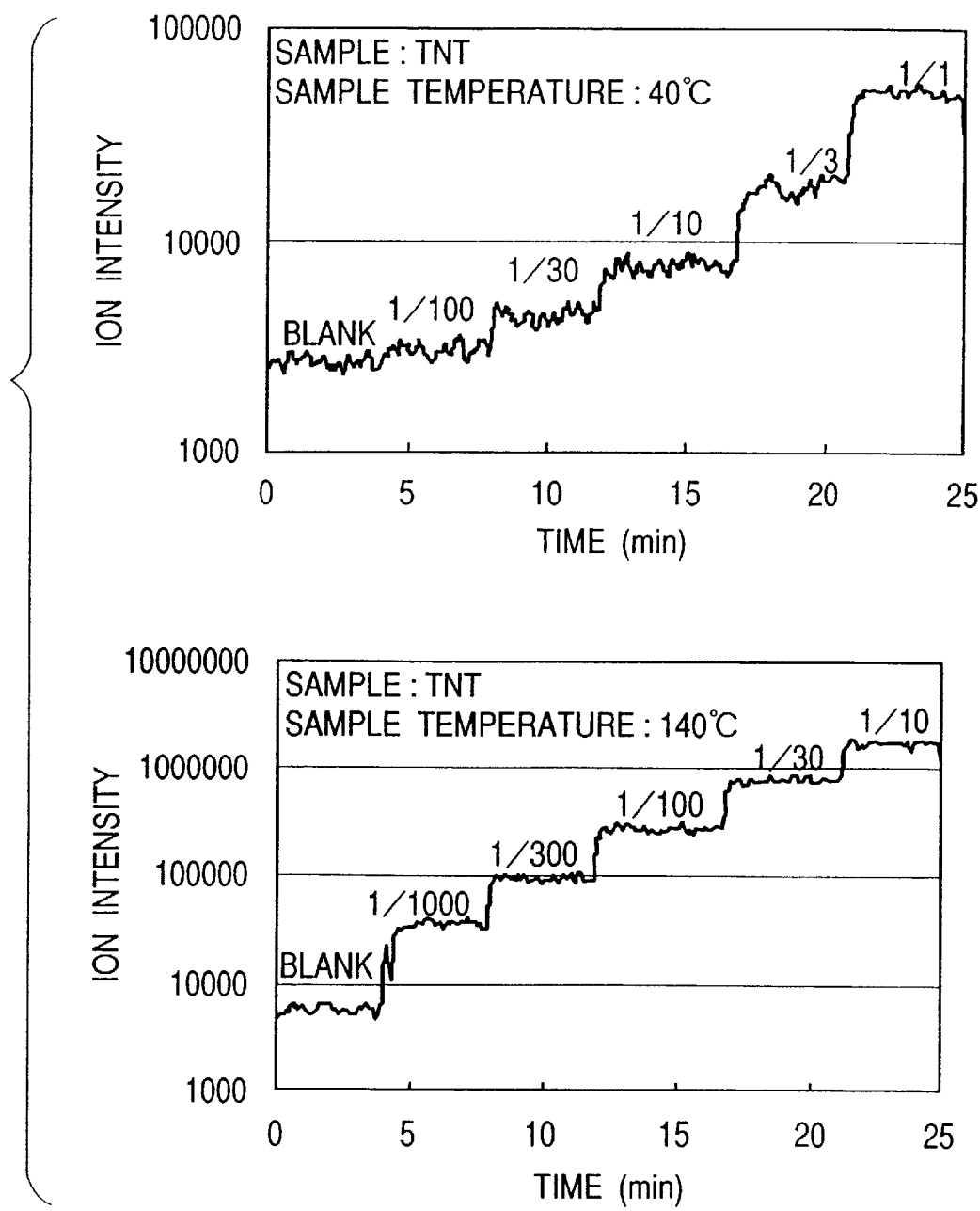
FIG. 23 illustrates graphs showing the relationship between the dilution ratio of TNT vapor and ion intensity.

The importance of raising the temperature of the sample to be detected can be understood from results shown in FIGS. 22 and 23. FIG. 22 shows the relationship between the temperature of a sample (TNT) and the ion intensity, and FIG. 23 shows the change in the ion intensity obtained by diluting vapor in the cases wherein the temperatures of the samples are different. When the temperature of the sample itself rises, its ion intensity rises abruptly. The ion intensities at room temperature and at 140° C. are different by two figures or more. As shown in FIG. 23, therefore, a sample having a high temperature can be detected even when the sample itself is highly diluted. The significance of the solid sample heater 21 in FIGS. 9 and 10 falls within this point.

Embodiment 2

Figure 2:
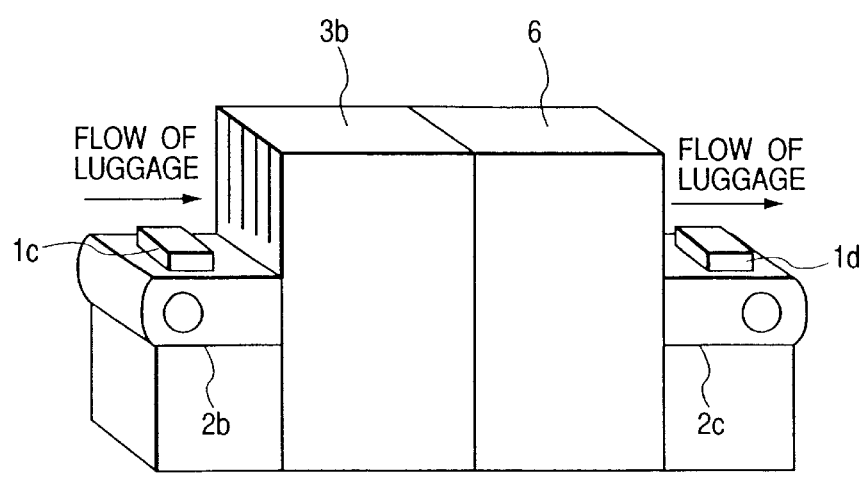
FIG. 2 is a diagrammatic perspective view of an explosive detection system of the present invention.

FIG. 2 is a view illustrating another embodiment of the explosive detection system of the present invention. In the present embodiment, which is different from the embodiment illustrated in FIG. 1, a gas is automatically and continuously sucked from luggage or the like, which is carried on a belt conveyor and then analyzed, and it is determined from results of the analysis whether an explosive is present or not. In this case, an X-ray inspection system may be used at the same time.

Figure 3:
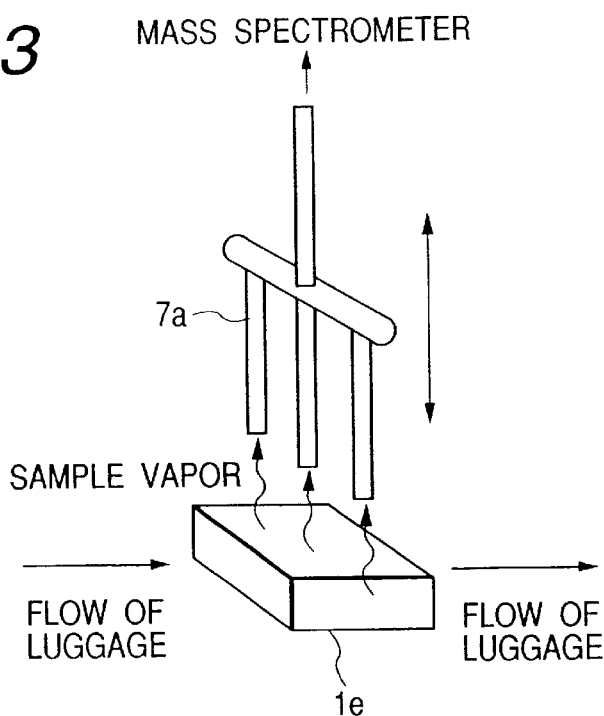
FIG. 3 is a diagrammatic view of a vapor sucking region.
Figure 4:
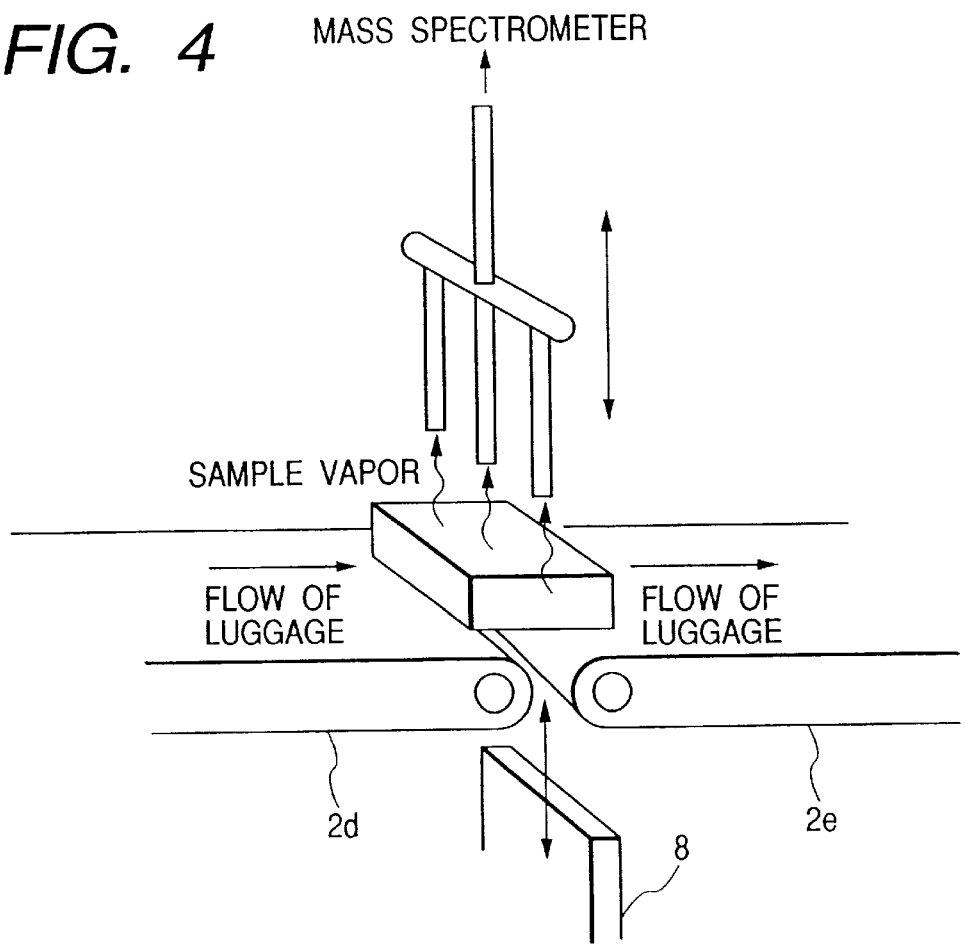
FIG. 4 is a diagrammatic view of a vapor sucking region.

The details of the present embodiment will be specifically described, with reference to FIG. 2 and the like. Luggage and the like are inspected in public facilities such as an airport and a port at the time of embarkation. An object 1c to be inspected, such as a bag, is carried on a belt conveyor 2b to an X-ray inspection system 3b. The luggage which is subjected to an inspection for explosives which have metal components is inspected by an explosive detection system 6 for on-line analysis for the purpose of detecting the vapor of explosives. As illustrated in FIG. 3, in this system 6 an inspector uses a sampling probe 7a for on-line analysis, which probe has openings or gaps near an object 1e to be inspected, such as the bag, to suck vapor leaking from the object 1e to be inspected, and forwards it to an analyzing region. In this case, as shown in FIG. 4, an object pressing device 8 for pressing any object to be inspected may be located between belt conveyors 2d and 2e to increase the amount of the vapor leaking from the object 1e. This device 8 is a device for pressing any object to be inspected at the time of sampling vapor to detect an explosive so as to promote the discharge of the vapor. The pressure against the object to be inspected is effective not only in the case where it is performed upwards, as illustrated in FIG. 4, but also in the case where it is performed in the right and left directions. The inspector checks a detection result through an indicating device 64 as shown in FIG. 24. The indicating device 64 has an indicator 65 for a substance corresponding to an ion to be detected. If, for example, substance "A" is detected, the fact that substance "A" is detected is indicated by turning on and off the indicator "A" according to the above-mentioned algorithm. In this case, it is permissible to simultaneously provide an indicator 66 and an alarm 67 for indicating the degree of concentration being detected. (As simple information, information as to whether the amount is large or small is permissible.)

Figure 27:
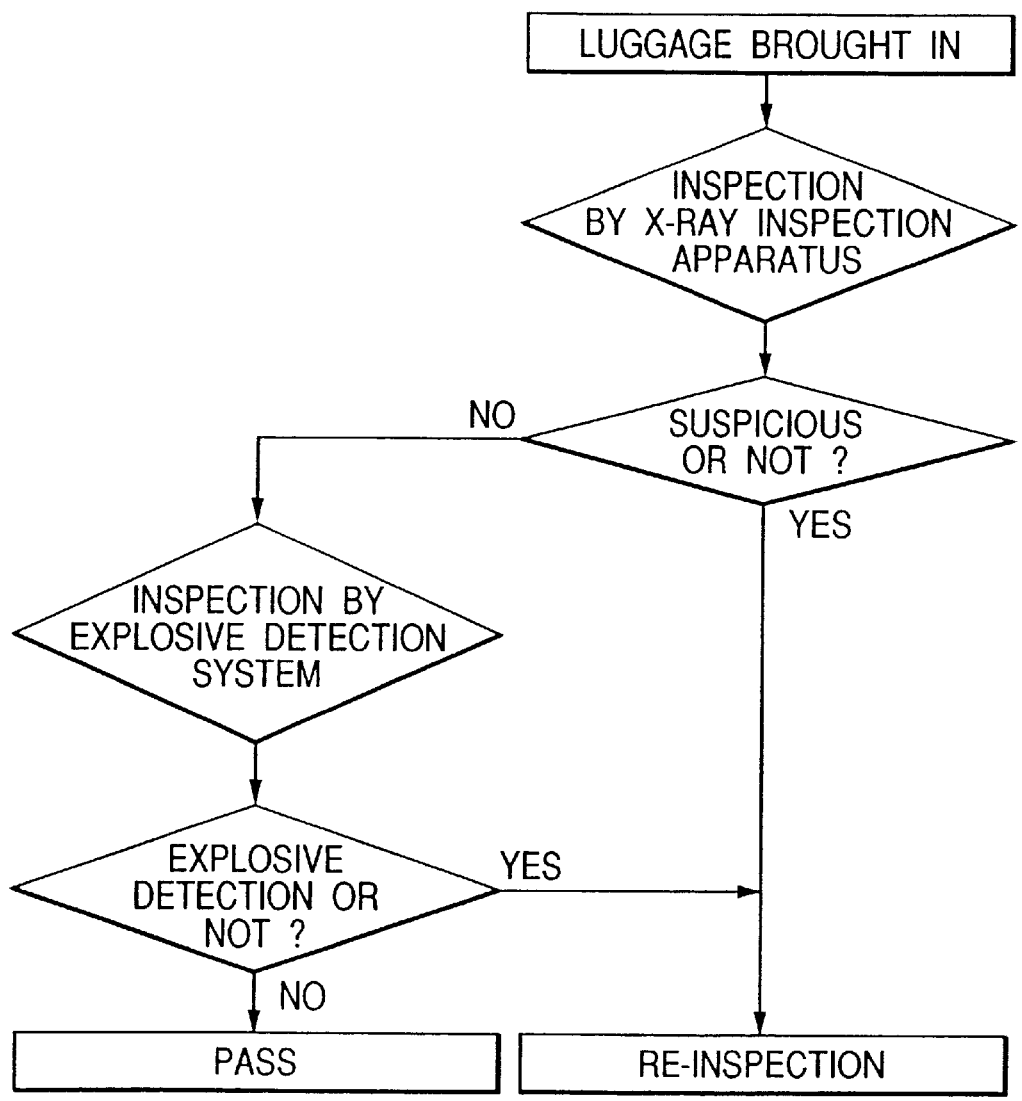
FIG. 27 is a flowchart of an operation of an on-line explosive detection system combined with an X-ray inspection system.

A flowchart for such an inspection described as above is shown in FIG. 27. When no abnormality is detected by the X-ray inspection system 3b, nor the explosive detection system 6 for on-line analysis, the luggage is permitted to pass. When an abnormality is detected, a close re-inspection is made.

The manner of sampling the sample gas from the luggage such as a trunk case is as follows. When the trunk case is carried on the belt conveyor, the trunk case is received inside the bottom portion of the conveyor, which is made up to have a concave form. The trunk case is covered with an upper cover, in synchronization with the advance of the belt conveyor. Within 1 second thereafter, the inside is subjected to a negative pressure by the pump, so that the sample gas inside the case is discharged outside. This discharged gas is inspected. Before the conveyor reaches a goal, the upper cover is taken off and then the trunk case on the concave bottom is taken off.

This procedure can be applied, without limitation to the time when the trunk case is moving. When the trunk case is received, the trunk case is stored in a room established for storing any trunk case and then the room is made up to a slightly negative pressure to collect the sample gas from the trunk case by a sampling device. The collected gas is detected in an analyzing region. The luggage can be quickly inspected without injuring the luggage by producing such a negative pressure and detecting the sample gas.

The same advantage as Embodiment 1 can be produced by adopting such an inspection system structure. In this case, all objects are inspected in both the X-ray inspection system and the explosive detection system. Therefore, the result, based on the X-ray inspection system and the result based on the explosive detection system can be combined for inspection, so as to raise the possibility of detecting explosives. Simultaneously, the inspector is not troubled so that the inspection can be effectively made.

Embodiment 3

FIG. 3 is a view illustrating still another embodiment of the explosive detection system of the present invention. In the present embodiment, an inspector sets a sampling probe into an opening which is present at a corner of a large piece of freight, such as a container, and a gas inside the freight is sucked for a certain time to analyze the gas. It is determined from the result of the analysis whether there is an explosive present or not. An X-ray inspection system may be used at the same time.

Figure 5:
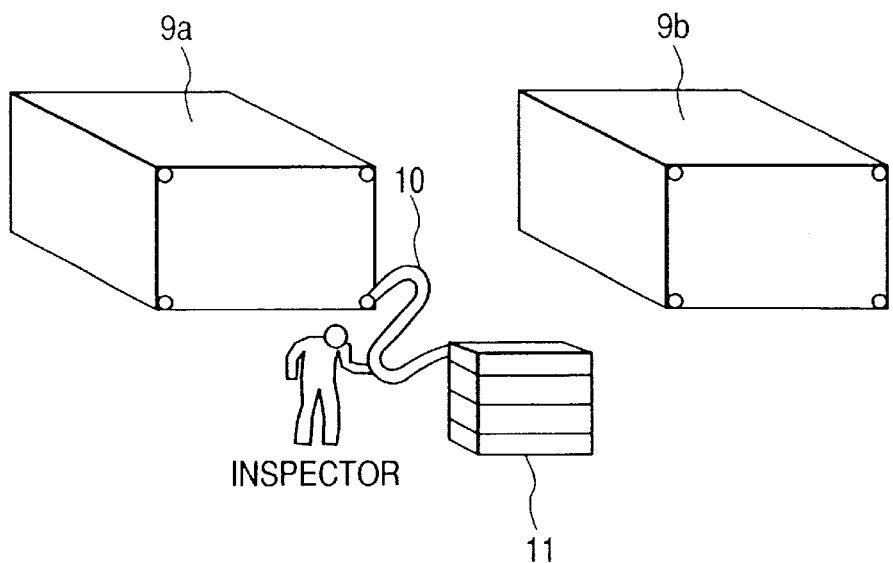
FIG. 5 is a diagrammatic view of an explosive detection system of the present invention.

The details of the present embodiment will be described with reference to FIG. 5 and the like. A large piece of freight, such as a container 9a or 9b, is inspected in public facilities such as an airport and a port. Concerning a large piece of freight such as a container 9a or 9b, a sampling probe 10 for analyzing containers is used to suck a gas inside the container from an opening which is present at a corner thereof. The gas is forwarded to an explosive detection system 11 for analyzing containers. In this case, openings other than the single opening may be closed, or the sampling may be simultaneously carried out from all openings. The inspector checks a detection result through an indicating device 64, as shown in FIG. 24. The indicating device 64 has an indicator 65 for a substance corresponding to an ion to be detected. If, for example, substance "A" is detected, the fact that substance "A" is detected is indicated by turning on and off the indicator "A" according to the above-mentioned algorithm. In this case, it is permissible to simultaneously provide an indicator 66 and an alarm 67 for indicating the degree of concentration being detected. (As simple information, information as to whether the amount is large or small is permissible.)

Figure 28:
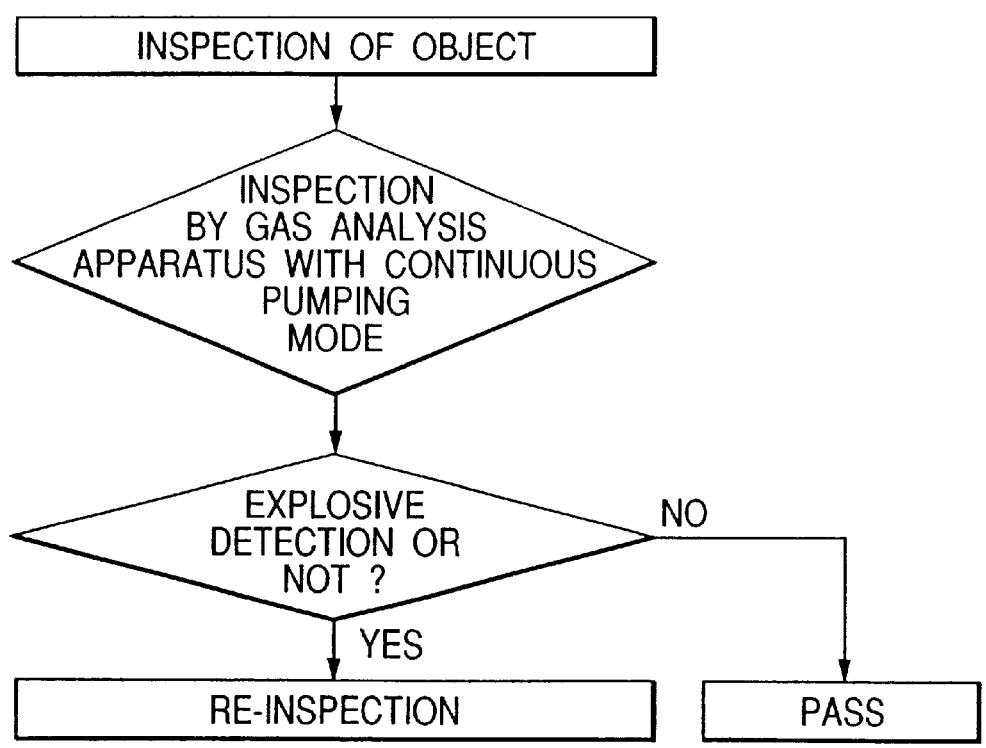
FIG. 28 is a flowchart of an operation of a walkthrough type explosive detection system.

A flowchart for such an inspection as described above is shown in FIG. 28. When no abnormality is detected by the explosive detection system 11 for analyzing containers, the luggage is permitted to pass. When an abnormality is detected, a close re-inspection is made.

According to such a system structure, in the case where an explosive is present in the container and its vapor leaks, the explosive can easily be detected and the safety of the container can be analyzed by the explosive detection system.

Embodiment 4

FIG. 4 is a view illustrating other embodiment of the explosive detection system of the present invention. In the present embodiment, a gas is sucked in for a certain time in, for example, a walk-in inspection apparatus in an atomic power plant, so as to analyze the gas. It is determined from the result of the analysis whether an explosive is present or not. A metal detection system or an X-ray inspection system can be used at the same time.

Figure 6:
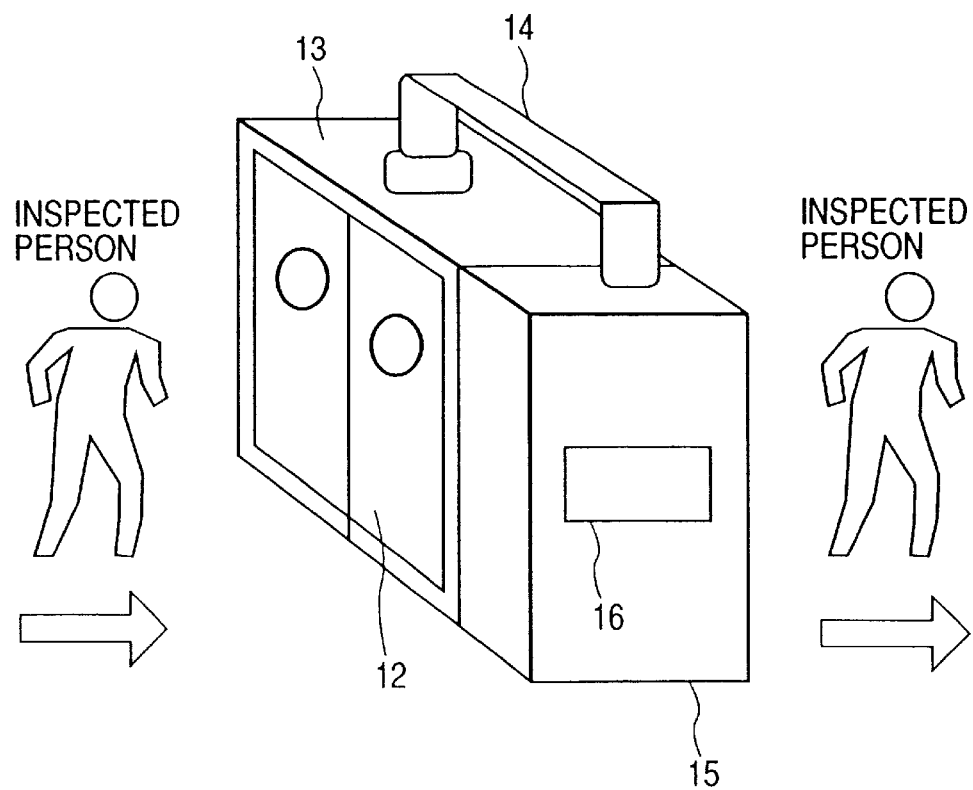
FIG. 6 is a diagrammatic perspective view of an explosive detection system of the present invention.

The details of the present embodiment will be described with reference to FIG. 6 and the like. In public facilities such as an atomic power plant, a walk-in inspection is made. At the walk-in inspection apparatus 12, a gas is collected from a person to be inspected for a certain time (from several seconds to several tens of seconds) in a vapor sampling room 13. The gas is forwarded through a vapor guide 14 to an explosive detection system 15 for the walk-in inspection apparatus, so as to analyze the gas. An inspector checks a detection result through a monitor of the explosive detection system 15. This monitor 16 has an indicator 65 for a substance corresponding to an ion to be detected. If, for example, a substance "A" is detected, the fact that substance "A" is detected is detected by turning on and off the indicator "A" according to the above-mentioned algorithm. In this case, it is permissible to simultaneously provide an indicator 66 and an alarm 67 for indicating the degree of concentration being detected. (As simple information, information as to whether the amount is large or small is permissible.)

Figure 29:
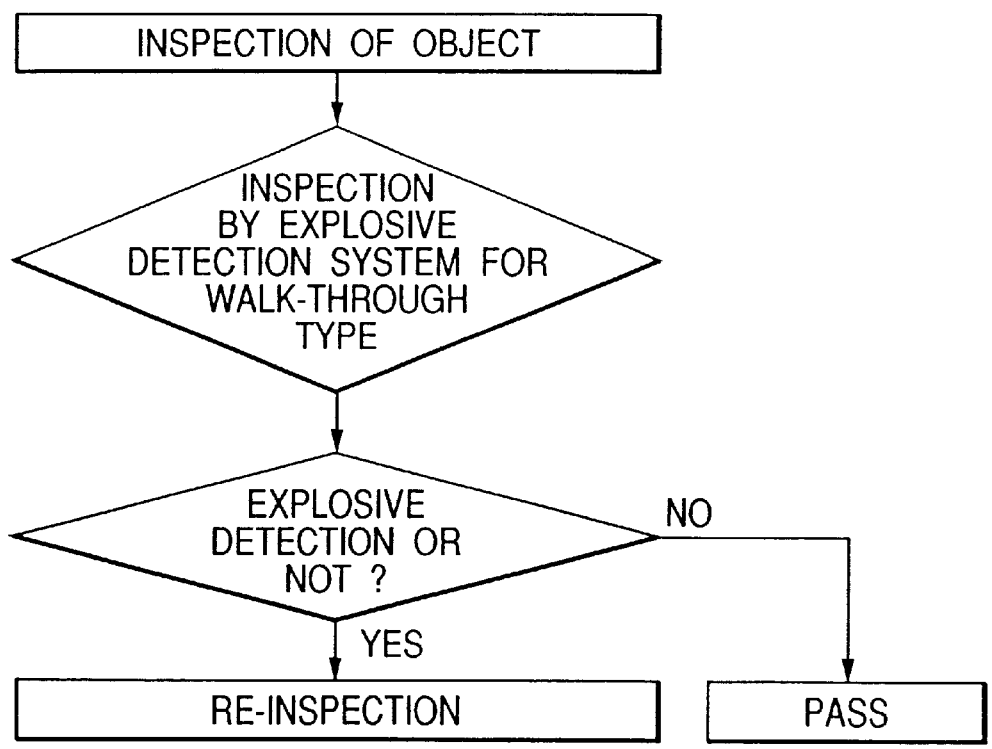
FIG. 29 is a flowchart of an operation of an explosive detection system for containers.

A flowchart for such an inspection as described above is shown in FIG. 29. When no abnormality is detected by the explosive detection system 15 the walk-in inspection apparatus, the person is permitted to pass. When an abnormality is detected, a close re-inspection is made.

According to such a system structure, in the case where an attempt is being made to bring an explosive into the plant, the explosive can be detected to block its entry.

Embodiment 5

When luggage is carried from an airport to an airplane, the luggage is carried by a carriage vehicle or car having a temperature adjuster for adjusting the temperature, a pressure adjuster for making negative pressure, a sampling means for sampling a sample gas, an ion trap mass spectrometer for ionizing the sampled gas and analyzing the gas, and an indicator for indicating the analyzed result. A detection of an explosive gas during the conveyance of luggage is made for every car, and thus the inspection is speedy.

The present invention described above makes it possible to detect an explosive which is put in a that is container substantially tight shut, for example, luggage such as a trunk case. In order to effectively detect, in particular, a small amount of a substance from which a vaporized gas is generated, the gas is effectively ionized and an ion trap mass spectrometer is used to make an inspection at a high speed. Thus, it becomes possible to judge whether there is an explosive or not in each of many carried pieces of luggage without opening the pieces of luggage. It also becomes possible to judge whether there is an explosive or not in a block unit, that is, in a unit of containers in which plural pieces of luggage are put, without inspecting the individual pieces. This makes an improvement of the detection speed possible. By using the present system together with a metal detection system or an X-ray inspection system, the detection sensitivity of an explosive can be made higher.

What is claimed is:

1. A sample introduction probe for introducing a gas sample to a mass spectrometer, comprising:

an inner pipe for conducting the sample to be analyzed;

an outer pipe installed outside of said inner pipe;

a member having a sample introduction port installed at one end of said inner pipe for enabling entry of the sample into said inner pipe;

a pump for introducing the sample from said sample introduction port to said inner pipe;

a probe tip heater for heating said member at said one end of said inner pipe;

a heater, which is independent of said probe tip heater, for heating said inner pipe;

a filter installed inside said inner pipe; and a clean-out port being formed at said member for cleaning said filter;

wherein said inner pipe is a flexible pipe and said outer pipe is a bendable pipe.

2. The sample introduction probe according to claim 1, wherein said heater is installed inside said inner pipe.

3. A sample introduction probe for introducing a gas sample to a mass spectrometer, comprising:

an inner pipe for conducting the sample to be analyzed;

an outer pipe installed outside of said inner pipe;

a member having a sample introduction port installed at one end of said inner pipe for enabling entry of the sample into said inner pipe;

a pump for introducing the sample from said sample introduction port to said inner pipe;

a probe tip heater for heating said member at said one end of said inner pipe;

a heater independent of said probe tip heater for heating said inner pipe; and a solid sample heating means installed on said member at said one end of said inner pipe and installed at one end of said outer pipe.

4. The sample introduction probe of claim 3, wherein said solid sample heating means is an infrared ray lamp.

5. The sample introduction probe of claim 3, wherein said solid sample heating means is a halogen lamp.

6. The sample introduction probe according to claim 3, wherein said heater is installed inside said inner pipe.

7. The sample introduction probe according to claim 3, further comprising:

a filter installed inside said inner pipe; and a clean-out port being formed at said member for cleaning said filter.

8. The sample introduction probe according to claim 3, wherein said inner pipe is a flexible pipe and said outer pipe is a bendable pipe.

9. A sample introduction probe for introducing gas sample to a mass spectrometer, comprising:

an inner pipe for conducting the sample to be analyzed;

an outer pipe installed outside of said inner pipe;

a member having a sample introduction port installed at one end of said inner pipe for enabling entry of the sample into said inner pipe;

a pump for introducing the sample from said sample introduction port to said inner pipe;

a probe tip heater for heating said member at said one end of said inner pipe;

a heater, which is independent of said probe chip heater for heating said inner pipe;

a filter installed inside said inner pipe;

a clean-out port being formed at said member for cleaning said filter;

a handle installed at said member for handling said sample introduction probe; and a switch for said pump installed at said member.

10. A sample introduction probe for introducing gas sample to a mass spectrometer, comprising:

an inner pipe for conducting the sample to be analyzed;

an outer pipe installed outside of said inner pipe;

a member having a sample introduction port installed at one end of said inner pipe for enabling entry of the sample into said inner pipe;

a pump for introducing the sample from said sample introduction port to said inner pipe;

a probe tip heater for heating said member at said one end of said inner pipe;

a heater, which is independent of said probe chip heater for heating said inner pipe;

a filter installed inside said inner pipe;

a clean-out port being formed at said member for cleaning said filter; and a handle installed at said member for handling said sample introduction probe.

* * * * *